US011039077B2

(12) United States Patent
Hirota

(10) Patent No.: US 11,039,077 B2
(45) Date of Patent: Jun. 15, 2021

(54) IMAGE PROCESSING DEVICE, ENDOSCOPE SYSTEM, IMAGE PROCESSING METHOD, AND COMPUTER-READABLE RECORDING MEDIUM

(71) Applicant: OLYMPUS CORPORATION, Tokyo (JP)

(72) Inventor: Masashi Hirota, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 56 days.

(21) Appl. No.: 16/660,014

(22) Filed: Oct. 22, 2019

(65) Prior Publication Data
US 2020/0053268 A1 Feb. 13, 2020

Related U.S. Application Data

(63) Continuation of application No. PCT/JP2017/016636, filed on Apr. 26, 2017.

(51) Int. Cl.
*H04N 5/235* (2006.01)
*G06T 7/50* (2017.01)
(Continued)

(52) U.S. Cl.
CPC ....... *H04N 5/2351* (2013.01); *A61B 1/00009* (2013.01); *A61B 1/045* (2013.01);
(Continued)

(58) Field of Classification Search
CPC .......... H04N 5/2351; H04N 2005/2255; G06T 7/50; G06T 3/40; G06T 5/002; G06T 2207/10068; G06T 7/586; G06T 2207/20152; A61B 1/00009; A61B 1/045; A61B 1/0638
(Continued)

(56) References Cited

U.S. PATENT DOCUMENTS

2015/0363932 A1 12/2015 Hirota et al.
2016/0089012 A1 3/2016 Aoyama

FOREIGN PATENT DOCUMENTS

JP 2013-146484 A 8/2013
JP 5393525 B2 1/2014
(Continued)

OTHER PUBLICATIONS

English abstract of JP 2011-167349 A.
International Search Report dated Jul. 4, 2017 received in PCT/JP2017/016636.

*Primary Examiner* — Matthew K Kwan
(74) *Attorney, Agent, or Firm* — Scully, Scott, Murphy & Presser, P.C.

(57) ABSTRACT

An image processing device includes: an image acquiring unit configured to acquire a plurality of images at different imaging time which images are captured when illumination light in different wavelength bands is emitted; and a processor including hardware. The processor is configured to generate a low-resolution image by lowering resolution of at least one image in the plurality of images, and detect light-absorption information at a certain depth based on a correlation between images which are in an image group including the low-resolution image and the plurality of images, which are captured with the illumination light in different wavelength bands, and at least one of which is the low-resolution image.

6 Claims, 17 Drawing Sheets

(51) Int. Cl.
*G06T 5/00* (2006.01)
*G06T 3/40* (2006.01)
*A61B 1/00* (2006.01)
*A61B 1/045* (2006.01)
*H04N 5/225* (2006.01)

(52) U.S. Cl.
CPC ............. *G06T 3/40* (2013.01); *G06T 5/002* (2013.01); *G06T 7/50* (2017.01); *G06T 2207/10068* (2013.01); *H04N 2005/2255* (2013.01)

(58) Field of Classification Search
USPC .......................................................... 348/68
See application file for complete search history.

(56) References Cited

FOREIGN PATENT DOCUMENTS

| | | | |
|---|---|---|---|
| JP | 2014-161627 | A | 9/2014 |
| JP | 2016-025530 | A | 2/2016 |
| JP | 2016-067777 | A | 5/2016 |

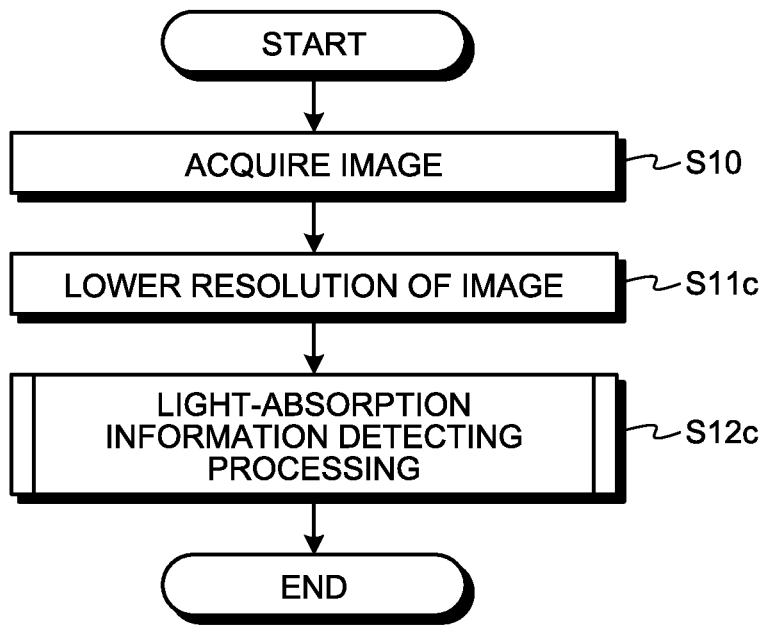
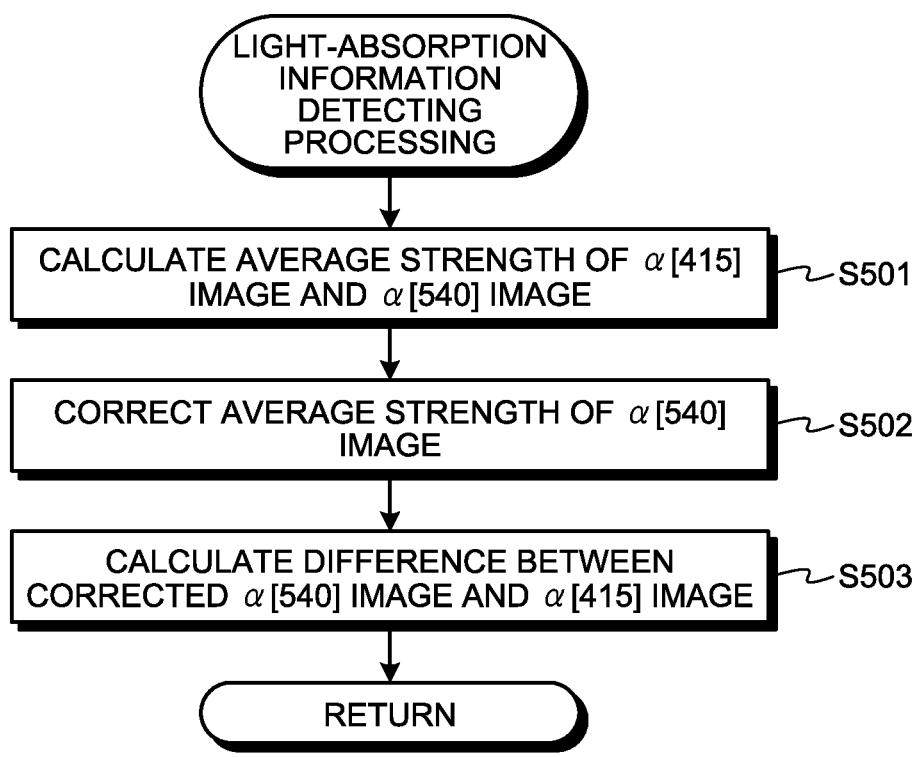

IMAGE PROCESSING DEVICE, ENDOSCOPE SYSTEM, IMAGE PROCESSING METHOD, AND COMPUTER-READABLE RECORDING MEDIUM

CROSS-REFERENCE TO RELATED APPLICATION

This application is a continuation of International Application No. PCT/JP2017/016636, filed on Apr. 26, 2017, the entire contents of which are incorporated herein by reference.

BACKGROUND

1. Technical Field

The present disclosure relates to an image processing device, an endoscope system, an image processing method, and a computer-readable recording medium to perform image processing with respect to a plurality of images acquired by capturing of an inside of a lumen of a living body.

2. Related Art

In the related art, an observation and a diagnosis of a living body (gastrointestinal tract) using an endoscope are widely performed. In an endoscopic diagnosis, it is considered that a blood vessel at a certain depth is preferably presented selectively according to a purpose of the diagnosis. For example, since cancer of a gastrointestinal tract often grows from a mucosa surface layer toward a lower layer, an observation of a blood vessel image specifically in the mucosa surface layer is important in screening of early cancer. Also, in a removal of a lesion, it is possible to previously prevent bleeding by presenting a thick artery in a mucosa deep layer. In Japanese Patent No. 5393525, a blood vessel at a certain depth is extracted on the basis of an interlayer between wavelengths in an endoscopic image in which three bands of RGB are serially captured (see Japanese Patent No. 5393525). According to this technology, a blood vessel in a living body surface layer is mainly extracted, and a blood vessel at a certain depth is extracted by utilization of a correlation between a B image with few blood vessels in a living body middle layer and a G image in which a blood vessel reflected in the living body middle layer is extracted.

SUMMARY

In some embodiments, an image processing device includes: an image acquiring unit configured to acquire a plurality of images at different imaging time which images are captured when illumination light in different wavelength bands is emitted; and a processor including hardware. The processor is configured to generate a low-resolution image by lowering resolution of at least one image in the plurality of images, and detect light-absorption information at a certain depth based on a correlation between images which are in an image group including the low-resolution image and the plurality of images, which are captured with the illumination light in different wavelength bands, and at least one of which is the low-resolution image.

In some embodiments, an endoscope system includes: an endoscope configured to generate image data by imaging an inside of a body of a subject when being inserted into the subject; and the image processing device configured to execute image processing with respect to an endoscopic image corresponding to the image data generated by the endoscope.

In some embodiments, an image processing method includes: acquiring a plurality of images at different imaging time which images are captured when illumination light in different wavelength bands is emitted; generating a low-resolution image by lowering resolution of at least one image in the plurality of images; and detecting light-absorption information at a certain depth based on a correlation between images which are in an image group including the low-resolution image and the plurality of images, which are captured with illumination light in different wavelength bands, and at least one of which is the low-resolution image.

In some embodiments, provided is a non-transitory computer-readable recording medium with an executable program stored thereon. The program causes an image processing device to execute: acquiring a plurality of images at different imaging time which images are captured when illumination light in different wavelength bands is emitted; generating a low-resolution image by lowering resolution of at least one image in the plurality of images; and detecting light-absorption information at a certain depth based a correlation between images which are in an image group including the low-resolution image and the plurality of images, which are captured with illumination light in different wavelength bands, and at least one of which is the low-resolution image.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 27 is a flowchart illustrating an outline of processing executed by the image processing device according to the third embodiment of the disclosure; and FIG. 28 is a flowchart illustrating an outline of light-absorption information detecting processing in FIG. 27.

DETAILED DESCRIPTION

In the following, an image processing device, an image processing method, and a program according to embodiments of the disclosure will be described with reference to the drawings. Note that the disclosure is not limited to these embodiments. Also, the same sign is assigned to identical parts in description of the drawings.

First Embodiment

Configuration of Image Processing Device

Figure 1:
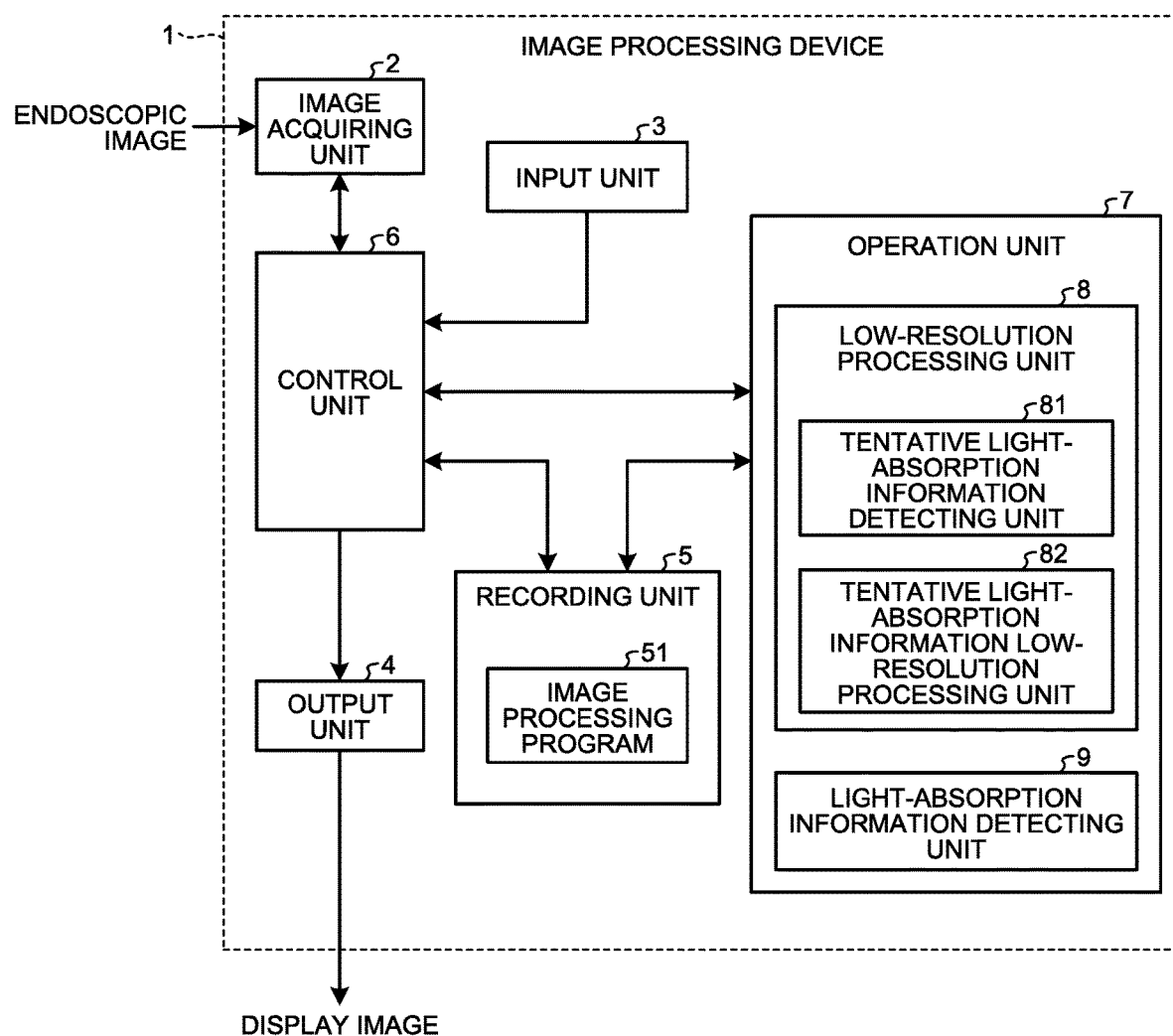
FIG. 1 is a block diagram illustrating a configuration of an image processing device according to a first embodiment of the disclosure.

FIG. 1 is a block diagram illustrating a configuration of an image processing device according to the first embodiment of the disclosure. An image processing device 1 according to the present first embodiment is a device that executes image processing to reduce an influence of a positional deviation and to detect light-absorption information of each endoscopic image with respect to an endoscopic image group (moving image data of inner lumen image group) including a temporally-successive plurality of endoscopic images (inner lumen image) acquired by successive imaging of a lumen of a living body, to which lumen light in a predetermined wavelength band is emitted, by an endoscope (scope of endoscope such as flexible endoscope or rigid endoscope) or a capsule endoscope (hereinafter, these will be simply referred to as "endoscope" collectively), for example. Also, an endoscopic image (inner lumen image) is usually a color image having a pixel level (pixel value) with respect to a wavelength component of red (R), green (G), or blue (B) in each pixel position.

The image processing device 1 illustrated in FIG. 1 includes an image acquiring unit 2 that outputs, from an endoscope or the outside, an endoscopic image corresponding to image data captured by the endoscope, an input unit 3 that receives an input signal input by operation from the outside, an output unit 4 that outputs a display image or various kinds of information to the outside or a display device, a recording unit 5 that records the endoscopic image output by the image acquiring unit 2 and various programs, a control unit 6 that controls an operation of the whole image processing device 1, and an operation unit 7 that performs predetermined image processing with respect to an image.

The image acquiring unit 2 is configured arbitrarily according to a form of a system including an endoscope. For example, in a case where a portable recording medium is used for delivery of image data with respect to an endoscope, the image acquiring unit 2 is configured as a reader device to which this recording medium is detachably attached and which reads recorded image data. Also, in a case where a server that records image data captured by an endoscope is used, the image acquiring unit 2 includes a communication device or the like that can communicate with this server bi-directionally, and acquires the image data by performing data communication with the server. Moreover, the image acquiring unit 2 may include an interface device or the like to which image data is input from an endoscope through a cable.

The input unit 3 is realized by an input device such as a keyboard, a mouse, a touch panel, or various switches, and outputs an input signal received in response to operation from the outside to the control unit 6.

Under control by the control unit 6, the output unit 4 outputs information or an image extracted by an operation by the operation unit 7 to a display device connected by wired connection, a display device connected by wireless communication, or the like. Note that the output unit 4 includes a liquid-crystal or organic electro luminescence (EL) display panel, or the like and may display various images including an image on which image processing is performed by the operation by the operation unit 7 or may output warning with a sound or a character.

The recording unit 5 is realized by various IC memories such as a flash memory, a read only memory (ROM), and a random access memory (RAM), a hard disk built inside or connected by a data communication terminal, and the like. In addition to image data or moving image data acquired by the image acquiring unit 2, the recording unit 5 records a program to operate the image processing device 1 and to make the image processing device 1 execute various functions, and data or the like used during execution of this program. For example, the recording unit 5 lowers resolution of at least one image among a plurality of images, and records an image processing program 51 to detect light-absorption information at a certain depth and various kinds of information and the like used during execution of this program on the basis of a correlation between the plurality of images including the image resolution of which is lowered.

The control unit 6 includes a general-purpose processor such as a central processing unit (CPU) or a special-purpose processor such as various operation circuits, which are to execute a certain function, such as an application specific integrated circuit (ASIC) and a field programmable gate array (FPGA). In a case of being a general-purpose processor, for example, the control unit 6 transfers an instruction or data is transferred to each unit included in the image processing device 1 by reading various programs stored in the recording unit 5, and integrally controls an operation of the whole image processing device 1. Also, in a case where the control unit 6 is a special-purpose processor, the processor may independently execute various kinds of processing, or the processor and the recording unit 5 may execute various kinds of processing in cooperation or in combination by using the various kinds of data or the like stored in the recording unit 5.

The operation unit 7 includes a general-purpose processor such as a CPU or a special-purpose processor such as various operation circuits that are an ASIC, an FPGA, and the like and that execute a certain function. In a case of being a general-purpose processor, the operation unit 7 detects light-absorption information at a certain depth on the basis of an acquired endoscopic image by reading the image processing program 51 from the recording unit 5. Also, in a case where the operation unit 7 is a special-purpose processor, the processor may independently execute various kinds of processing, or the processor and the recording unit 5 may execute processing in cooperation or in combination by using the various kinds of data or the like stored in the recording unit 5.

Detailed Configuration of Operation Unit

Next, a detailed configuration of the operation unit 7 will be described.

The operation unit 7 includes a low-resolution processing unit 8 and a light-absorption information detecting unit 9.

The low-resolution processing unit 8 generates a low-resolution image by lowering resolution of at least one image among a plurality of images which is acquired by the image acquiring unit 2 and which has different imaging time and different wavelength bands of light. The low-resolution processing unit 8 includes a tentative light-absorption information detecting unit 81 that detects tentative light-absorption information from an image in a certain wavelength band, and a tentative light-absorption information low-resolution processing unit 82 that lowers resolution of tentative light-absorption information.

The light-absorption information detecting unit 9 detects light-absorption information at a certain depth on the basis of a correlation between a plurality of images that is a plurality of images at least including a low-resolution image and that has different wavelength bands of light.

Processing of Image Processing Device

Figure 2:
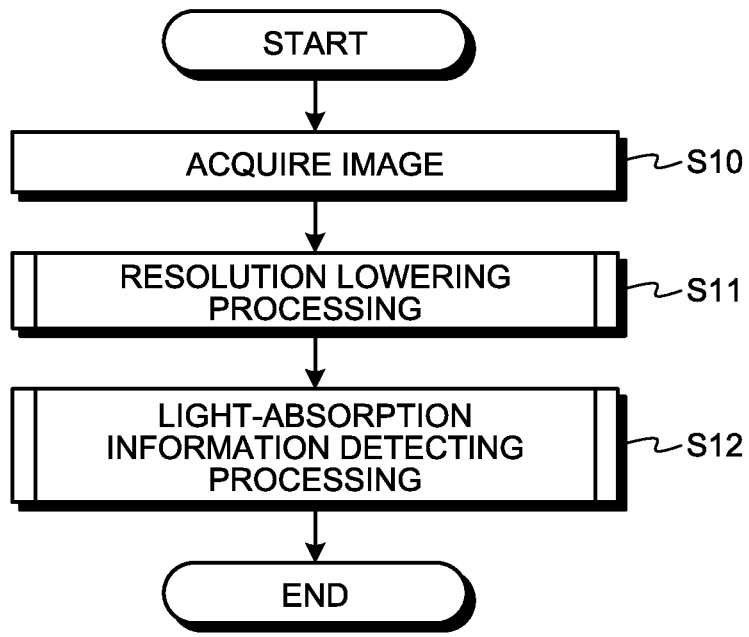
FIG. 2 is a flowchart illustrating an outline of processing executed by the image processing device according to the first embodiment of the disclosure.

Next, processing executed by the image processing device 1 will be described. FIG. 2 is a flowchart illustrating an outline of processing executed by the image processing device 1.

Figure 4:
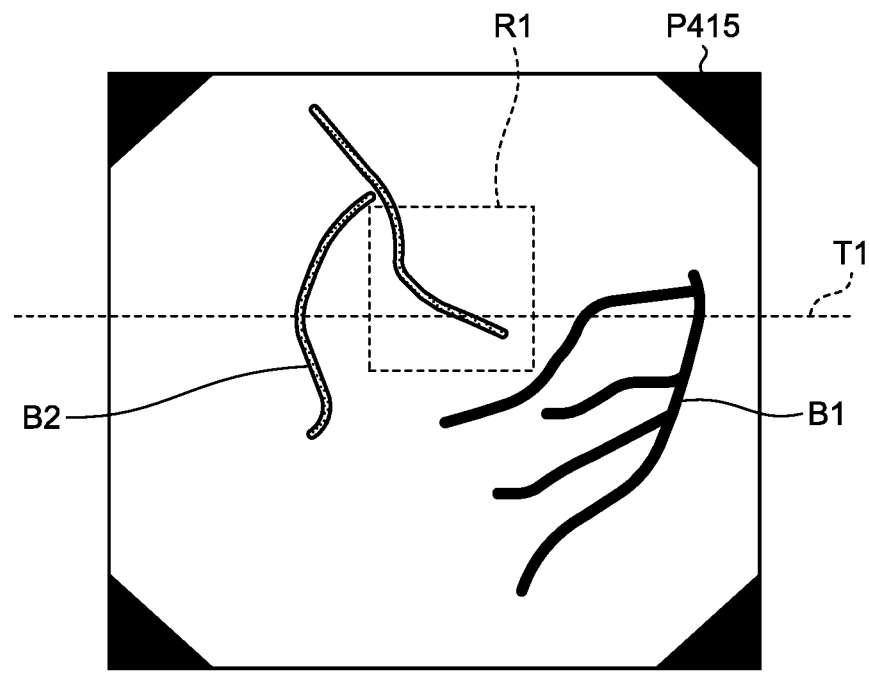
FIG. 4 is a view illustrating an example of a narrowband image with a center wavelength being 415 nm.
Figure 5:
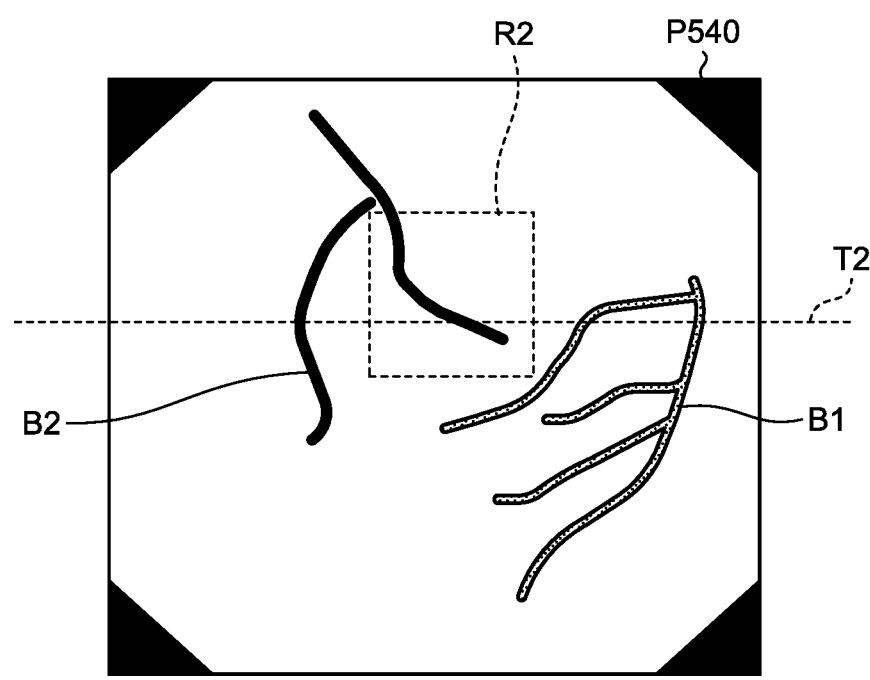
FIG. 5 is a view illustrating an example of a narrowband image with a center wavelength being 540 nm.

As illustrated in FIG. 2, first, the image acquiring unit 2 acquires, from an endoscope or the outside, a plurality of images that has different imaging time and that is captured when illumination light in different wavelength bands is emitted (step S10). Here, an image that captures any one of a gastrointestinal tract, a blood vessel, and an organ is included in the plurality of images. Also, illumination light of when the plurality of images is captured is illumination light by a light emitting diode (LED) light source and is illumination light intentionally limited to a predetermined wavelength band. More specifically, the image acquiring unit 2 acquires two narrowband images with a center wavelength being 415 nm or 540 nm (such as narrowband image captured with illumination light having wavelength band of 395 nm to 445 nm and narrowband image captured with illumination light having wavelength band of 530 nm to 550 nm) from an endoscope or the outside. More specifically, as illustrated in FIG. 4 and FIG. 5, the image acquiring unit 2 acquires a narrowband image P415 with a center wavelength being 415 nm, and a narrowband image P540 with a center wavelength of 540 nm. As illustrated in FIG. 4 and FIG. 5, each of the narrowband image P415 and the narrowband image P540 includes a superficial blood vessel B1 and a middle-layer blood vessel B2.

Note that an imaging method of the above-described two narrowband images is not limited to an LED light source and may be, for example, illumination light by a laser light source or illumination light by a combination of a white light source and a band-limiting filter. Also, a detection object and a wavelength band are not limited to the above-described two wavelength bands. For example, with light-absorption information in a deep layer as an object, an image in a long wavelength region with a center wavelength being 600 nm (narrowband image captured with illumination light having wavelength band of 585 nm to 615 nm) or an image in a long wavelength region with a center wavelength being 670 nm (narrowband image captured with illumination light having wavelength band of 610 nm to 730 nm) may be acquired from an endoscope or the outside. In the following description, a narrowband image with a center wavelength being 415 nm is described as a [415] image and a narrowband image with a center wavelength being 540 nm is described as a [540] image. Moreover, in the following, the [415] image is described as an example of an image in which light-absorption information at a certain depth appears in the highest contrast.

Here, the light-absorption information is image information indicating a light absorption change that appears in a narrowband image when narrowband light used for capturing of the narrowband image is absorbed by a light absorber in an object. A light absorption change that appears in a narrowband image varies depending on an absorption and scattering property of narrowband light. For example, since narrowband light with a center wavelength in the vicinity of 415 nm is easily absorbed by hemoglobin, when an absorption amount of the narrowband light is increased in a blood vessel or a blood vessel proliferation region in which a blood current including hemoglobin flows, a light absorption change appears in a narrowband image. A pixel position of this region in which light absorption changes, and a value indicating an amount of the light absorption change in the narrowband light in the pixel position are included in the light-absorption information. Since the narrowband light is absorbed and luminance is decreased in the region in which the light absorption changes, a value indicating the amount of the light absorption change becomes a negative value. A value indicating the amount of the light absorption change becomes small as an absorption amount in a light absorption band by the light absorber becomes large. That is, an absolute value becomes large. For example, in a case where an object is captured with illumination light with a center wavelength being any one of 415 nm, 460 nm, and 540 nm, an image in which a blood vessel in a submucosal layer appears in the highest contrast becomes the [415] image. In such a manner, the [415] image becomes an image in which light-absorption information (superficial blood vessel) to be detected appears in the highest contrast.

Subsequently, the low-resolution processing unit 8 executes resolution lowering processing of lowering resolution of the plurality of images acquired by the image acquiring unit 2 in step S10 described above (step S11).

Resolution Lowering Processing

Figure 3:
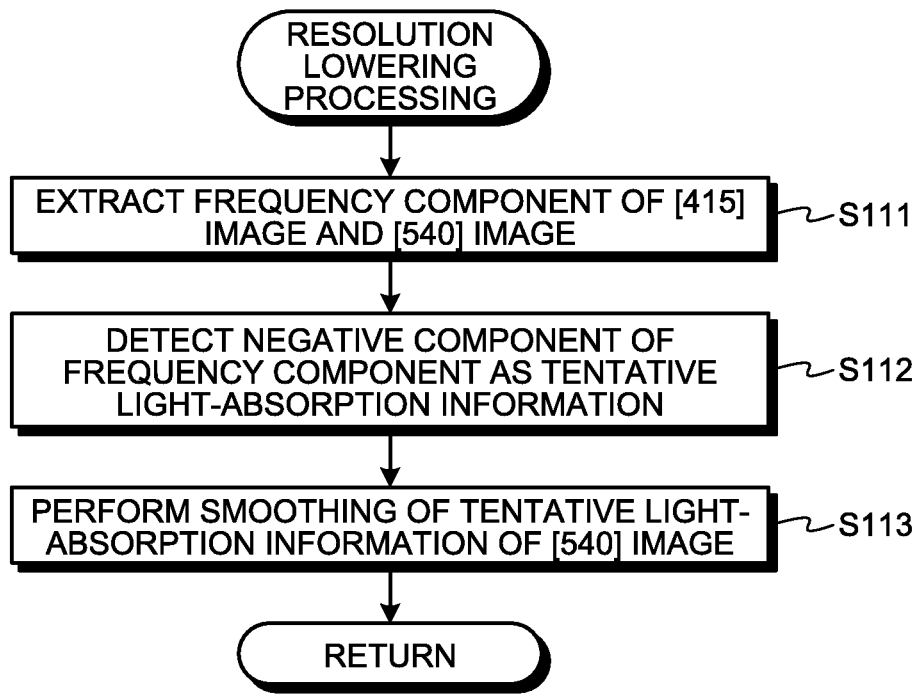
FIG. 3 is a flowchart illustrating an outline of resolution lowering processing in FIG. 2.

FIG. 3 is a flowchart illustrating an outline of resolution lowering processing in step S11 in FIG. 2. As illustrated in FIG. 3, first, the tentative light-absorption information detecting unit 81 extracts frequency components of the [415] image and the [540] image (step S111). More specifically, the tentative light-absorption information detecting unit 81 extracts a frequency component of each of the [415] image and the [540] image by applying a bandpass filter to each of the [415] image and the [540] image.

Figure 6:
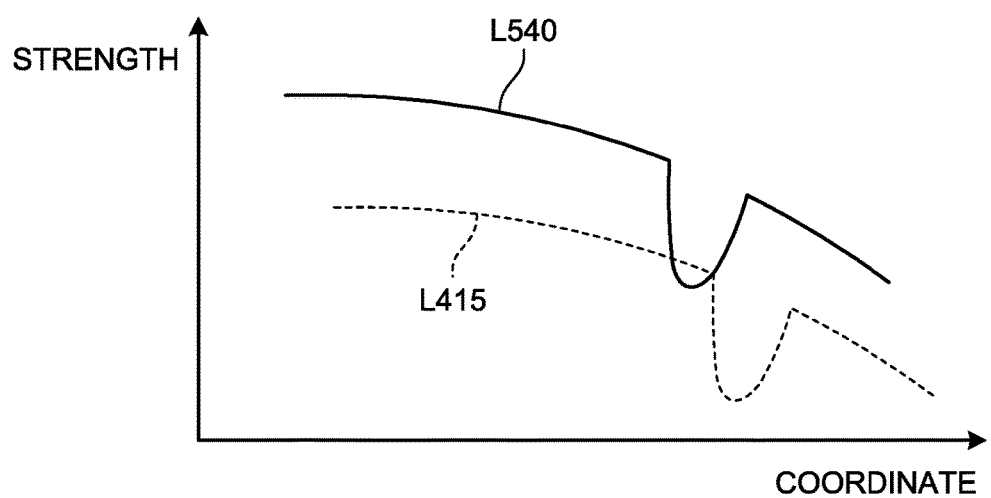
FIG. 6 is a view schematically illustrating strength of a pixel on a dotted line in a region in each of the narrowband image in FIG. 4 and the narrowband image in FIG. 5.
Figure 7:
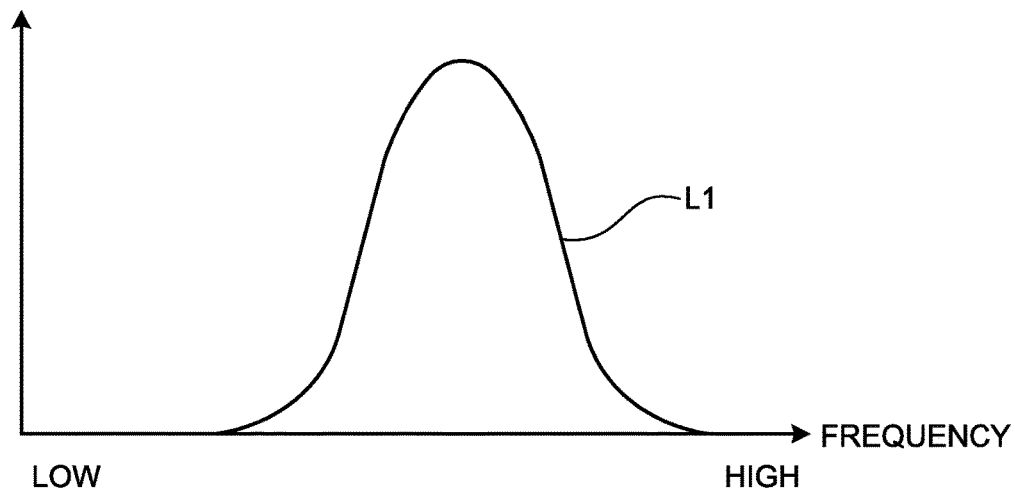
FIG. 7 is a view illustrating a transmission property of a bandpass filter applied by a tentative light-absorption information detecting unit according to the first embodiment of the disclosure.
Figure 8:
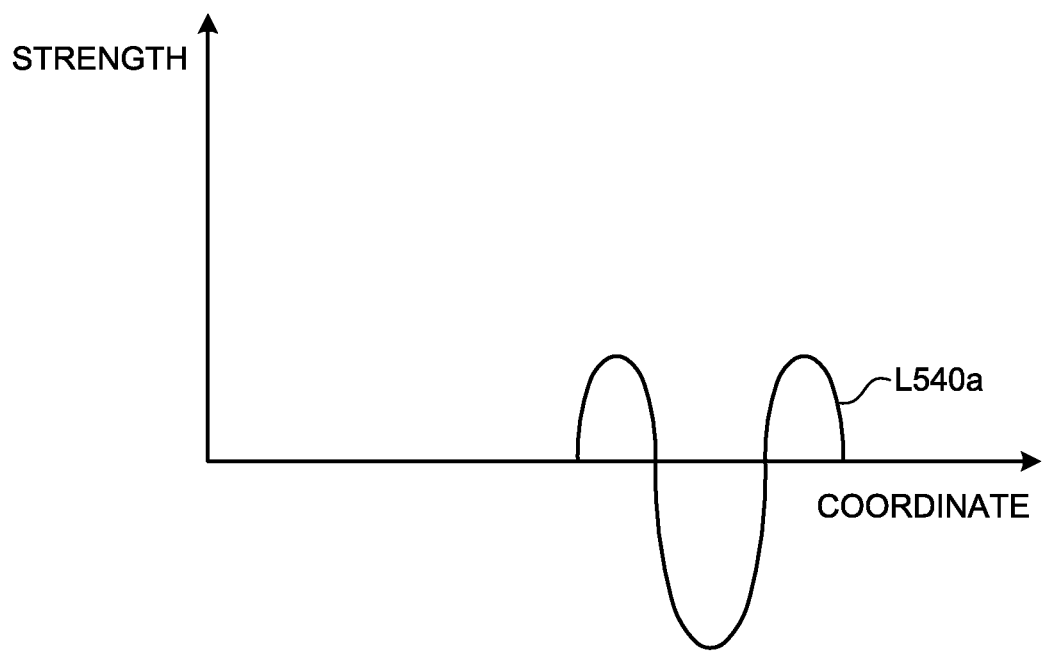
FIG. 8 is a view schematically illustrating strength of a pixel on a dotted line in FIG. 5 after the tentative light-absorption information detecting unit according to the first embodiment of the disclosure applies the bandpass filter to a [540] image.

FIG. 6 is a view schematically illustrating strength of a pixel on dotted lines T1 and T2 respectively in the narrowband image P415 in FIG. 4 and the narrowband image P540 in FIG. 5. As illustrated in FIG. 6, a horizontal axis indicates a coordinate (pixel position), a vertical axis indicates strength, a curved line L415 indicates a relationship between a coordinate and strength in a dotted line T1 in a region R1 in the narrowband image P415, and a curved line L540 indicates a relationship between the coordinate and the strength on a dotted line T2 in a region R2 in the narrowband image P540. FIG. 7 is a view illustrating a transmission property of the bandpass filter applied by the tentative light-absorption information detecting unit 81. In FIG. 7, a curved line L1 indicates a transmission property of the bandpass filter, and a horizontal axis indicates a frequency (low-frequency wave→high-frequency wave). FIG. 8 is a view schematically illustrating strength of a pixel on the dotted line T2 in FIG. 5 after the tentative light-absorption information detecting unit 81 applies the bandpass filter to the [540] image. In FIG. 8, a horizontal axis indicates a coordinate (pixel position), a vertical axis indicates strength, and a curved line L540a indicates a relationship between the coordinate and the strength after the bandpass filter is applied.

As illustrated in FIG. 6 to FIG. 8, by applying s bandpass filter having a property of the curved line L1 illustrated in FIG. 7 to each of the [415] image and the image, the tentative light-absorption information detecting unit 81 extracts a frequency component of each of the [415] image and the [540] image (for example, curved line L540 illustrated in FIG. 6→curved line L540a illustrated in FIG. 8).

Subsequently, the tentative light-absorption information detecting unit 81 detects a negative component of a frequency component as tentative light-absorption information (hereinafter, referred as "tentative light-absorption information") (step S112). More specifically, the tentative light-absorption information detecting unit 81 detects, as tentative light-absorption information, negative components of the frequency components in the image and the [540] image which frequency components are extracted in step S111 described above.

Figure 9:
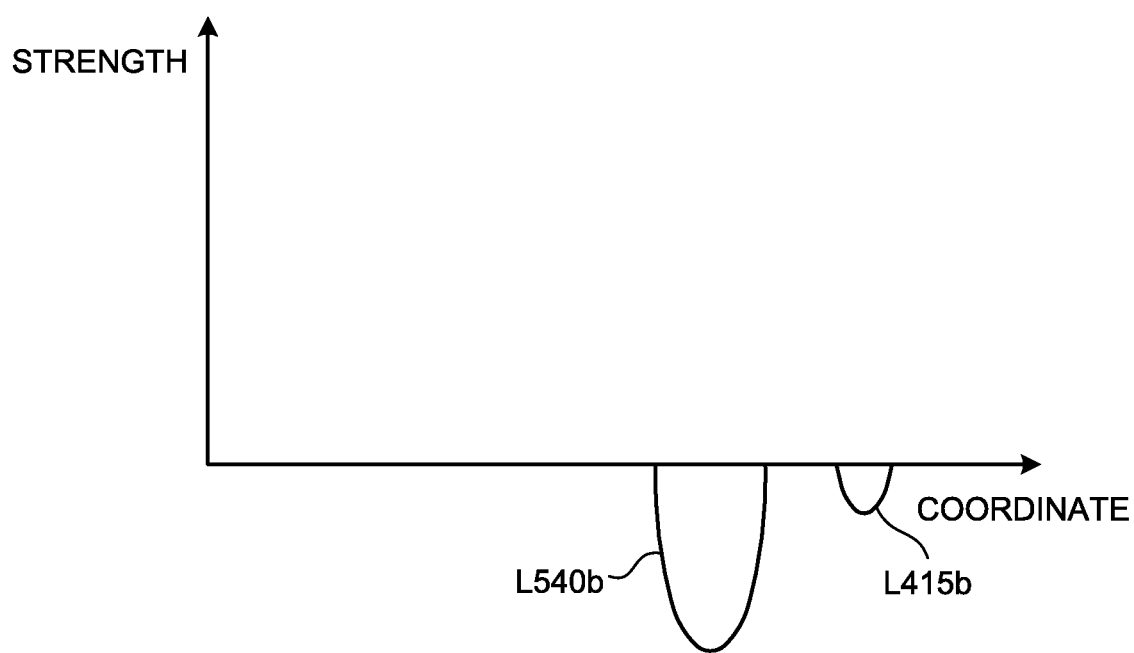
FIG. 9 is a view schematically illustrating tentative light-absorption information detected from each of a [415] image and the [540] image on dotted lines in FIG. 4 and FIG. 5 by the tentative light-absorption information detecting unit according to the first embodiment of the disclosure.
Figure 10:
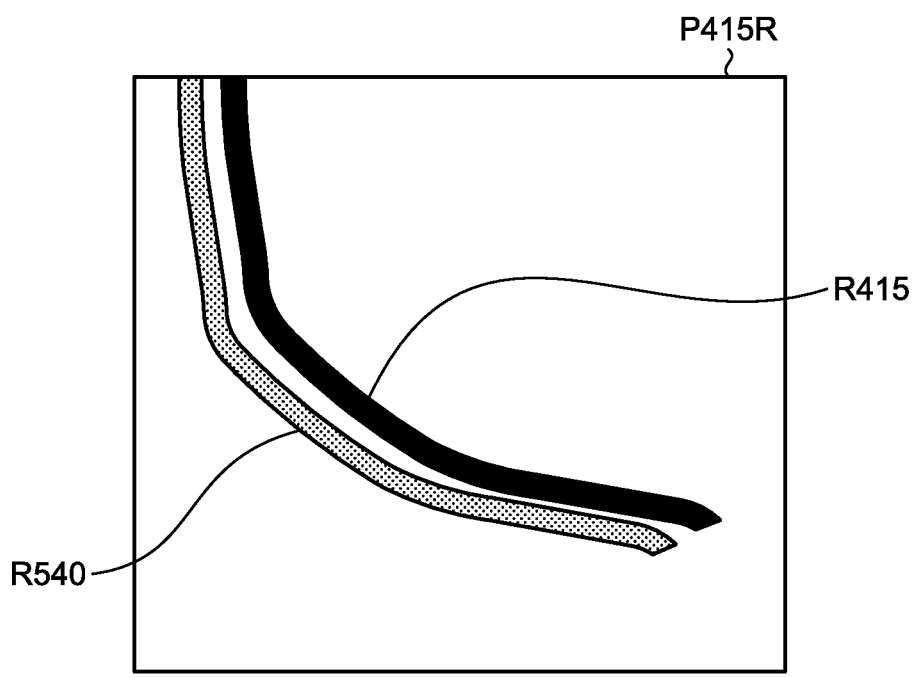
FIG. 10 is a view schematically illustrating the tentative light-absorption information detected from a region in FIG. 4 by the tentative light-absorption information detecting unit according to the first embodiment of the disclosure.

FIG. 9 is a view schematically illustrating tentative light-absorption information detected by the tentative light-absorption information detecting unit 81 respectively from the [415] image and the [540] image on the dotted lines T1 and T2 in the regions R1 and R2 in FIG. 4 and FIG. 5. In FIG. 9, a horizontal axis indicates a coordinate (pixel position), a vertical axis indicates strength, a curved line L540b indicates tentative light-absorption information of the [540] image, and a curved line L415b indicates tentative light-absorption information of the image. FIG. 10 is a view schematically illustrating the tentative light-absorption information detected by the tentative light-absorption information detecting unit 81 from the region R1 in FIG. 4. In an image P415R in FIG. 10, a region R415 indicates the tentative light-absorption information of the [415] image, and a region R540 indicates the tentative light-absorption information of the [540] image.

As illustrated in FIG. 9 and FIG. 10, the tentative light-absorption information detecting unit 81 detects, as the tentative light-absorption information of the [415] image and the [540] image, negative components of frequencies that respectively appear in the [415] image and the [540] image to which a bandpass filter having a property of the curved line L1 illustrated in FIG. 7 is applied.

Subsequently, the tentative light-absorption information low-resolution processing unit 82 generates a low-resolution image by smoothing the tentative light-absorption information of the [540] image (step S113).

Figure 11:
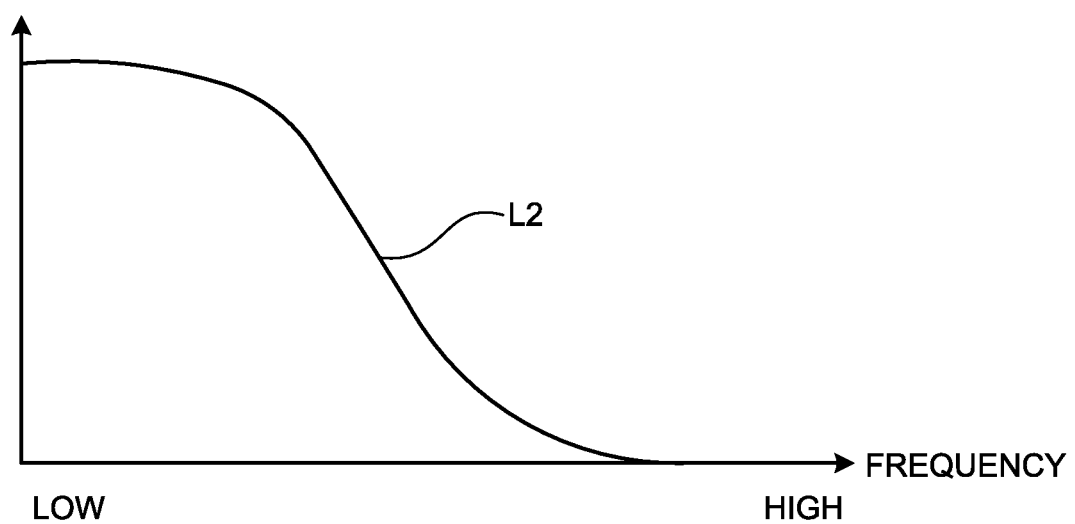
FIG. 11 is a view illustrating a property of a bandpass filter applied for smoothing by a tentative light-absorption information low-resolution processing unit according to the first embodiment of the disclosure.
Figure 12:
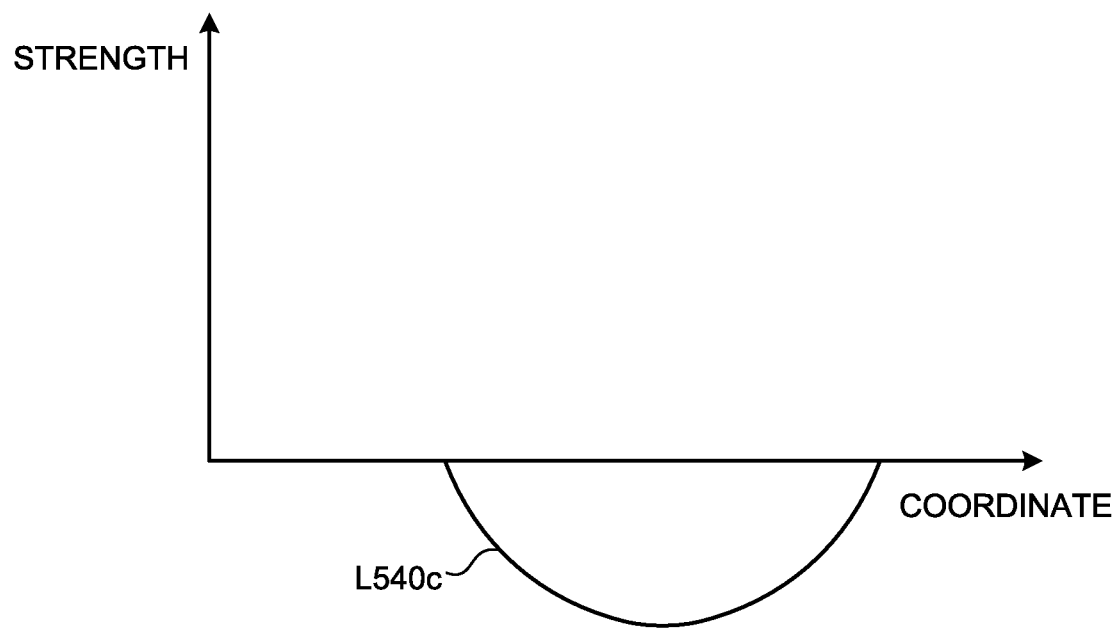
FIG. 12 is a view schematically illustrating a state in which the tentative light-absorption information detected from the [540] image is smoothed by the tentative light-absorption information low-resolution processing unit according to the first embodiment of the disclosure.
Figure 13:
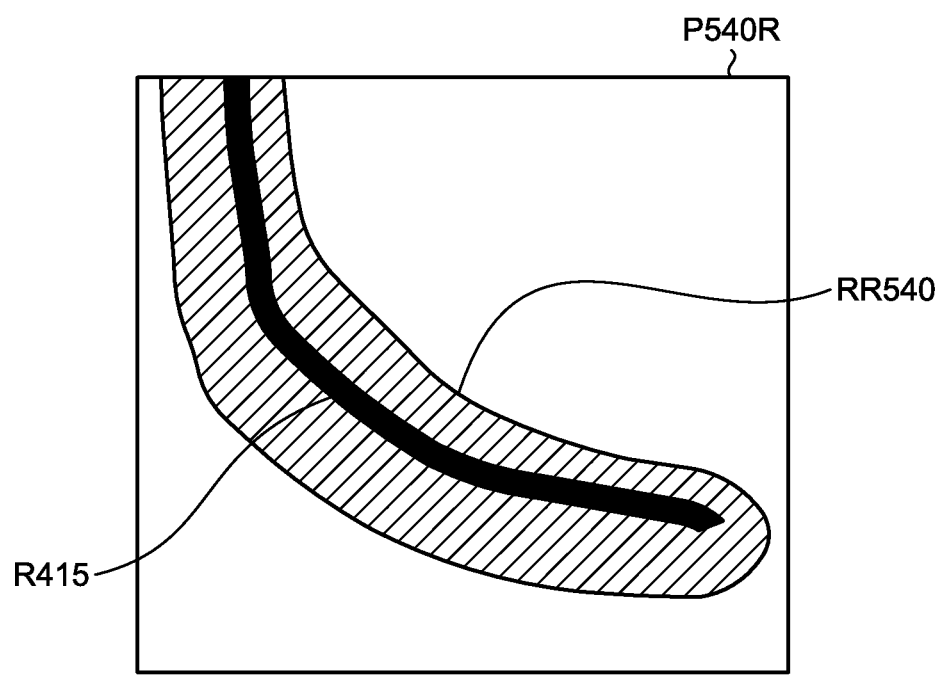
FIG. 13 is a view illustrating a state in which the tentative light-absorption information detected from the image is smoothed by the tentative light-absorption information low-resolution processing unit according to the first embodiment of the disclosure.

FIG. 11 is a view illustrating a property of a bandpass filter applied for smoothing by the tentative light-absorption information low-resolution processing unit 82. In FIG. 11, a curved line L2 indicates a property of the bandpass filter and a horizontal axis indicates a frequency (low-frequency wave→high-frequency wave). FIG. 12 is a view schematically illustrating a state in which the tentative light-absorption information detected from the [540] image is smoothed by the tentative light-absorption information low-resolution processing unit 82. In FIG. 12, a horizontal axis indicates a coordinate (pixel position), a vertical axis indicates strength, and a curved line L540c indicates a state in which the tentative light-absorption information detected from the [540] image is smoothed. FIG. 13 is a view illustrating a state in which the tentative light-absorption information detected from the [540] image is smoothed by the tentative light-absorption information low-resolution processing unit 82. In an image P540R in FIG. 13, a region R415 indicates the tentative light-absorption information of the [415] image, and a region RR540 indicates the smoothed tentative light-absorption information of the [540] image.

The tentative light-absorption information low-resolution processing unit 82 generates a low-resolution image by performing smoothing of the tentative light-absorption information of the [540] image as indicated by the curved line L540c illustrated in FIG. 12 by using a bandpass filter having a property of the curved line L2 illustrated in FIG. 11 with respect to the tentative light-absorption information of the [540] image which information is detected in step S112. More specifically, as illustrated in FIG. 13, the tentative light-absorption information low-resolution processing unit 82 generates the image P540R having the region RR540 by performing smoothing of the tentative light-absorption information detected from the [540] image. In the following description, a [540] image resolution of which is lowered is described as an α[540] image. After step S113, the image processing device 1 returns to a main routine in FIG. 2.

Referring back to FIG. 2, a description in and after step S11 will be continued.

In step S12, the light-absorption information detecting unit 9 executes light-absorption information detecting processing of detecting light-absorption information in a surface layer on the basis of a correlation between the [415] image and the α[540] image. After step S12, the image processing device 1 ends the present processing.

Outline of Light-Absorption Information Detecting Processing

Figure 14:
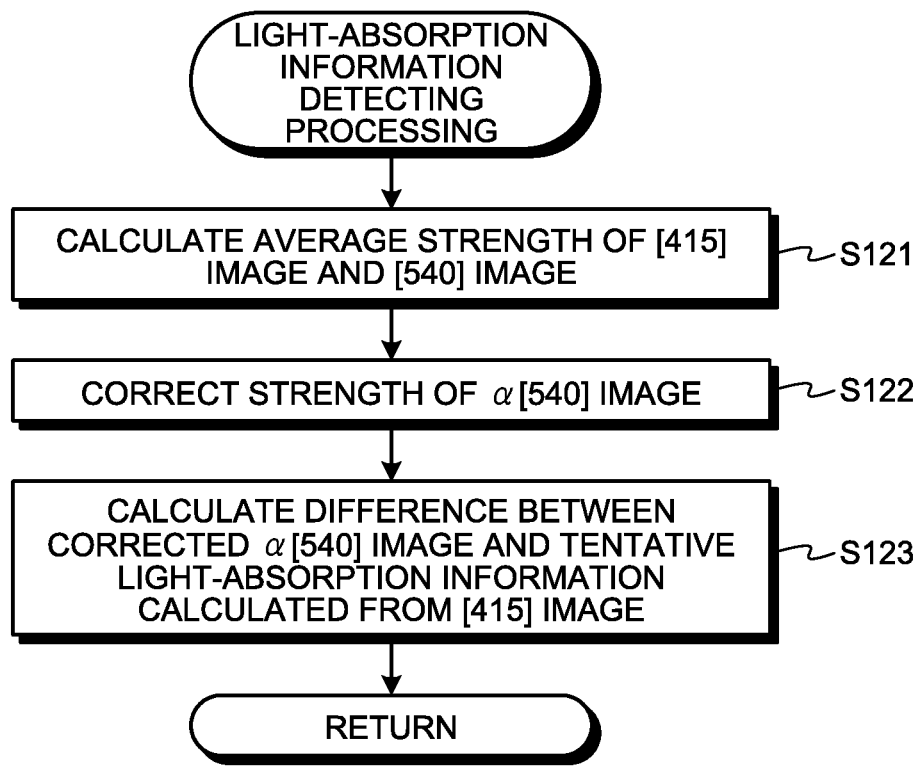
FIG. 14 is a flowchart illustrating an outline of light-absorption information detecting processing in FIG. 2.

FIG. 14 is a flowchart illustrating an outline of the light-absorption information detecting processing in step S12 in FIG. 2. As illustrated in FIG. 14, first, the tentative light-absorption information low-resolution processing unit 82 calculates average strength of the [415] image and the [540] image (step S121). In the tentative light-absorption information calculated from each of the image and the [540] image, relative strength varies due to an influence of light quantity, or the like during acquisition of an image (during imaging by endoscope). Thus, it is necessary to perform correction (normalization) in such a manner that a correlation between images can be calculated without an influence by light quantity or the like. Thus, the tentative light-absorption information low-resolution processing unit 82 calculates average strength of the [415] image and the [540] image.

Subsequently, the tentative light-absorption information low-resolution processing unit 82 corrects strength of the α[540] image (step S122). More specifically, the tentative light-absorption information low-resolution processing unit 82 corrects strength of the α[540] image by multiplying the α[540] image by a ratio β of average strength of the [415] image with respect to average strength of the [540] image (β=average strength of [415] image/average strength of [540] image) (α[540] image×β).

Figure 15:
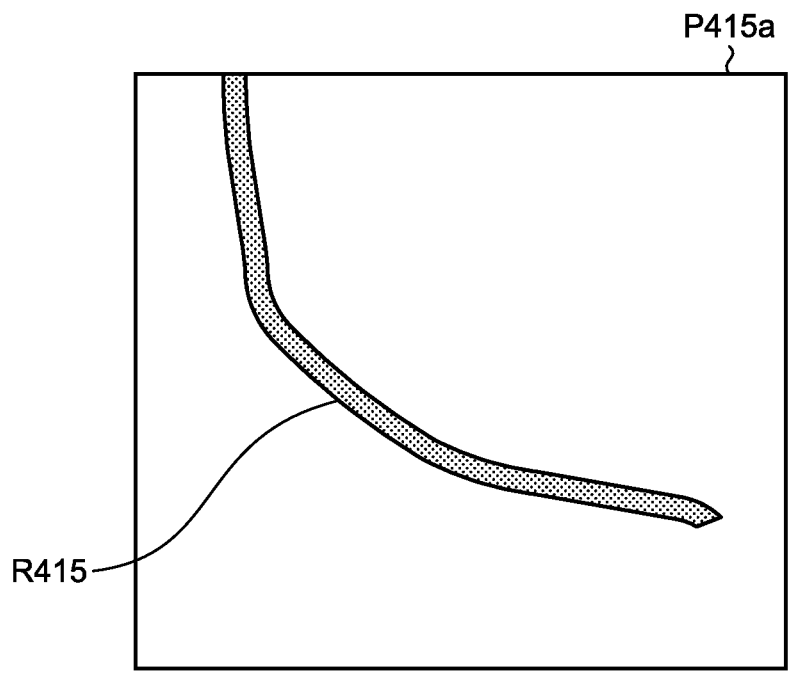
FIG. 15 is a view schematically illustrating an example of a [415] image after subtraction in the region in FIG. 4.
Figure 16:
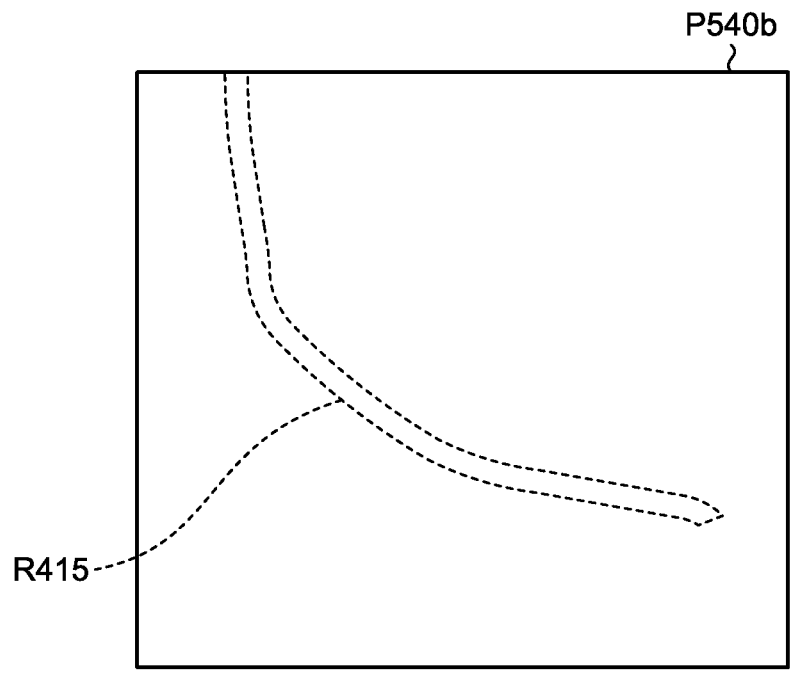
FIG. 16 is a view schematically illustrating an example of a [540] image after subtraction in the region in FIG. 4.
Figure 17:
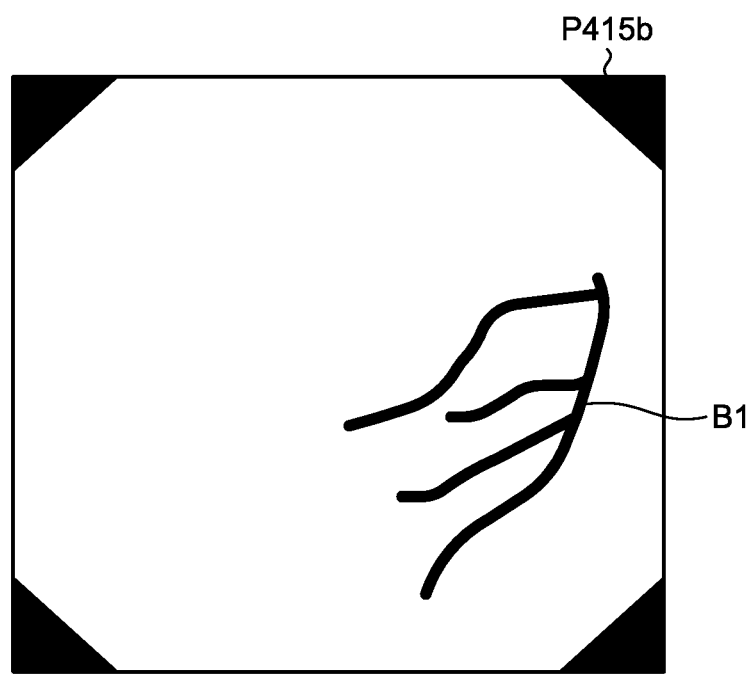
FIG. 17 is a view schematically illustrating an example of the [540] image after the subtraction.

Subsequently, the tentative light-absorption information low-resolution processing unit 82 calculates a difference between the corrected α[540] image and the tentative light-absorption information calculated from the image in step S11 in FIG. 2 described above (step S123). More specifically, as indicated by the image P415a in FIG. 15 and the image P540b in FIG. 16, the tentative light-absorption information low-resolution processing unit 82 executes subtraction processing to subtract the α[540] image (region RR540 in FIG. 13 described above) from the tentative light-absorption information of the [415] image (region R415 in FIG. 15), and detects a negative component in a result of this subtraction as light-absorption information at a certain depth in a living body, that is, light-absorption information in a surface layer from which a middle-layer blood vessel is deleted (see FIG. 16). In this case, the tentative light-absorption information low-resolution processing unit 82 performs the subtraction processing only in a negative region of each of the [415] image and the α[540] image. As a result, detection from which an influence of a positional deviation is reduced can be performed. Moreover, as illustrated in FIG. 17, an image P415b only including a superficial blood vessel B1 can be acquired. After step S123, the image processing device 1 returns to the main routine in FIG. 2.

According to the first embodiment of the disclosure described above, it is possible to improve accuracy in detection of light-absorption information at a certain depth by using a correlation with light-absorption information resolution of which is lowered. Thus, it is possible to improve accuracy in detection of a blood vessel.

First Modification Example of First Embodiment

Next, the first modification example of the first embodiment of the disclosure will be described. The first modification example of the present first embodiment has a configuration different from that of the image processing device 1 according to the above-described first embodiment, and resolution lowering processing executed by the image processing device is different. More specifically, although tentative light-absorption information is simply smoothed in the above-described first embodiment, a weight of smoothing is controlled on the basis of a shape in a [415] image in the first modification example of the present first embodiment. In the following, after a configuration of the image processing device according to the first modification example of the present first embodiment is described, resolution lowering processing executed by the image processing device according to the first modification example of the present first embodiment will be described. Note that the same sign is assigned to a configuration identical to that of the image processing device 1 according to the first embodiment described above and a description thereof is omitted.

Configuration of Image Processing Device

Figure 18:
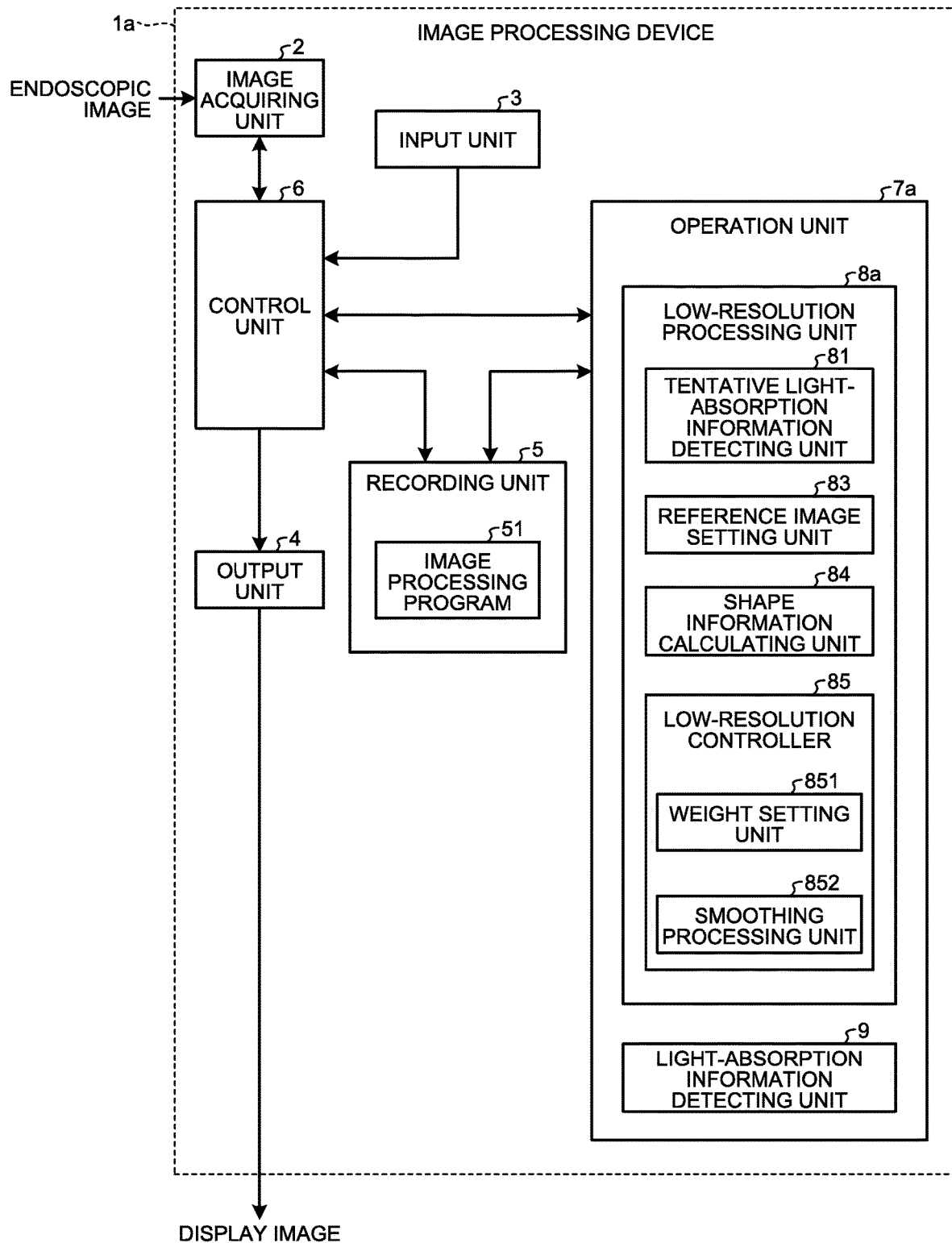
FIG. 18 is a block diagram illustrating a configuration of an image processing device according to a first modification example of the first embodiment of the disclosure.

FIG. 18 is a block diagram illustrating a configuration of the image processing device according to the first modification example of the first embodiment of the disclosure. An image processing device 1a illustrated in FIG. 18 includes an operation unit 7a instead of the operation unit 7 of the image processing device 1 according to the first embodiment described above. The operation unit 7a includes a general-purpose processor such as a CPU or a special-purpose processor such as various operation circuits that are an ASIC, an FPGA, and that like and that execute a certain function.

Detailed Configuration of Operation Unit

Next, a detailed configuration of the operation unit 7a will be described.

The operation unit 7a includes a low-resolution processing unit 8a and a light-absorption information detecting unit 9.

The low-resolution processing unit 8a generates a low-resolution image in which resolution of at least one image is lowered among a plurality of images that is acquired by an image acquiring unit 2 and that has different imaging time and different wavelength bands of light. The low-resolution processing unit 8a includes a tentative light-absorption information detecting unit 81, a reference image setting unit 83 that sets a reference image on the basis of a contrast of light-absorption information at a certain depth, a shape information calculating unit 84 that calculates shape information from each of a plurality of images including the reference image, and a low-resolution controller 85 that calculates shape information from each of the plurality of images including the reference image. Also, the low-resolution controller 85 includes a weight setting unit 851 that sets a weight in smoothing on the basis of a similarity between a shape of the reference image and shape information of an image other than the reference image, and a smoothing processing unit 852 that performs smoothing of the image other than the reference image on the basis of the weight.

Resolution Lowering Processing

Figure 19:
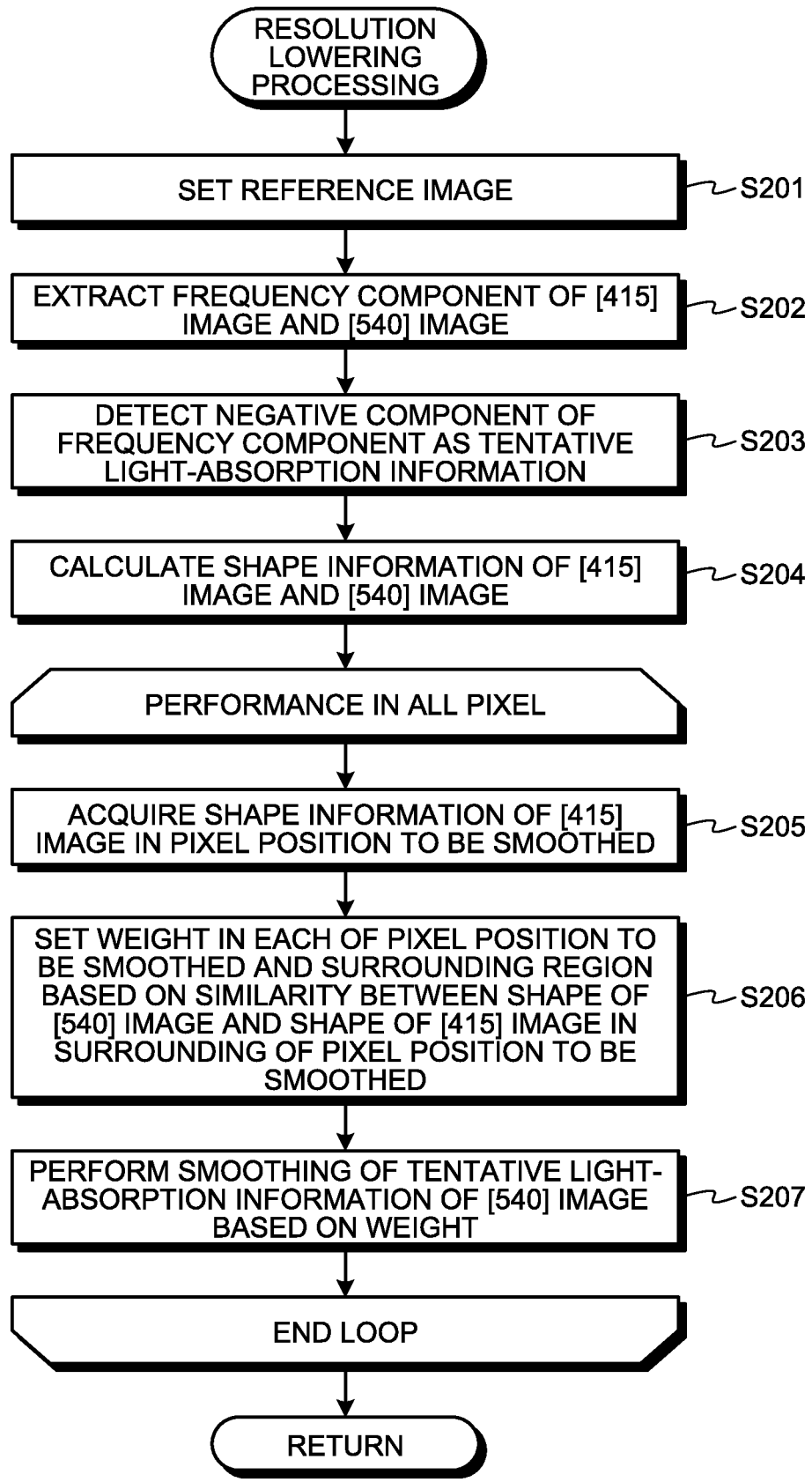
FIG. 19 is a flowchart illustrating an outline of resolution lowering processing executed by the image processing device according to the first modification example of the first embodiment of the disclosure.

Next, resolution lowering processing executed by the image processing device 1a will be described. FIG. 19 is a flowchart illustrating an outline of the resolution lowering processing executed by the image processing device 1a.

As illustrated in FIG. 19, the reference image setting unit 83 sets, as a reference image, any one of the plurality of images acquired by the image acquiring unit 2 (step S201). More specifically, the reference image setting unit 83 sets, as a reference image, a [415] image in which light-absorption information at a certain depth appears in the highest contrast among the plurality of images.

Since step S202 and step S203 respectively correspond to step S111 and step S112 in FIG. 3 described above, a description thereof is omitted.

In step S204, the shape information calculating unit 84 calculates shape information of each of a [415] image and a [540] image. For example, the shape information calculating unit 84 calculates an eigenvector in the Hessian matrices as shape information in all pixels of each of the [415] image and the [540] image. Note that the shape information calculating unit 84 may classify all pixels of each of the [415] image and the [540] image in an edge direction such as five kinds of directions that are a horizontal direction, a vertical direction, two diagonal directions, and a flat direction (no edge), and may calculate the classified edge directions as shape information.

Subsequently, the low-resolution controller 85 executes processing in step S205 to step S207 described in the following in all pixels. First, the low-resolution controller 85 acquires shape information of the [415] image in a pixel position to be smoothed (step S205).

Figure 20:
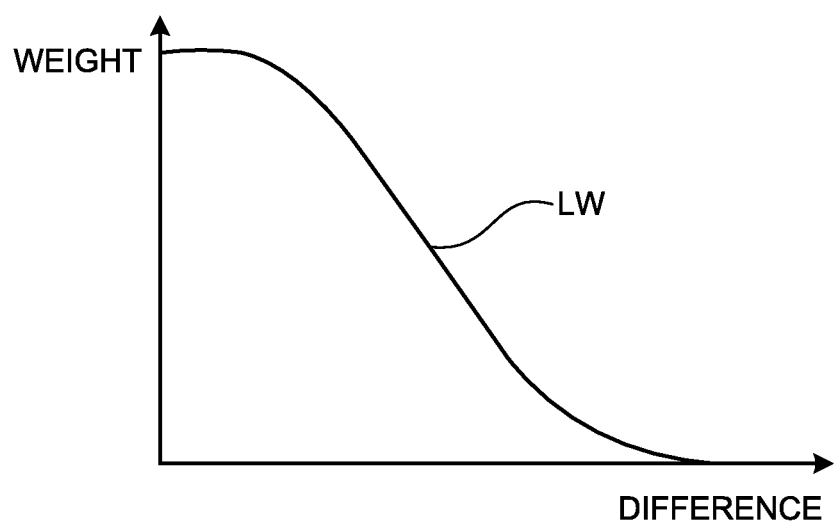
FIG. 20 is a view schematically illustrating a table in which a weight is set by setting unit according to the first modification example of the first embodiment of the disclosure.

Then, the weight setting unit 851 sets a weight in each of the pixel position to be smoothed and a surrounding region on the basis of a similarity between a shape of the [540] image and a shape of the [415] image in the surrounding of the pixel position to be smoothed (step S206). More specifically, the weight setting unit 851 sets a heavier weight in each pixel as a difference between the eigenvector of the [540] image and the eigenvector of the image in a pixel to be smoothed and each pixel in the surrounding becomes smaller. The weight setting unit 851 uses a table (function) set previously, for example, in a manner indicated by a curved line LW in FIG. 20.

Subsequently, the smoothing processing unit 852 performs smoothing of tentative light-absorption information of the [540] image on the basis of the weight set by the weight setting unit 851 (step S207). After step S207, the image processing device 1a returns to the main routine in FIG. 2.

According to the above-described first modification example of the first embodiment of the disclosure, it is possible to reduce an influence of a case where there is different light-absorption information in a surrounding by performing smoothing on the basis of a similarity in a shape. Thus, it is possible to improve accuracy in detection of light-absorption information at a certain depth in a living body.

Second Modification Example of First Embodiment

Next, the second modification example of the first embodiment of the disclosure will be described. An image processing device according to the second modification example of the present first embodiment executes different processing. In the following, processing executed by the second modification example of the present first embodiment will be described. Note that the same sign is assigned to a configuration identical to that of the image processing device 1 according to the first embodiment described above and a description thereof is omitted.

Processing of Image Processing Device

Figure 21:
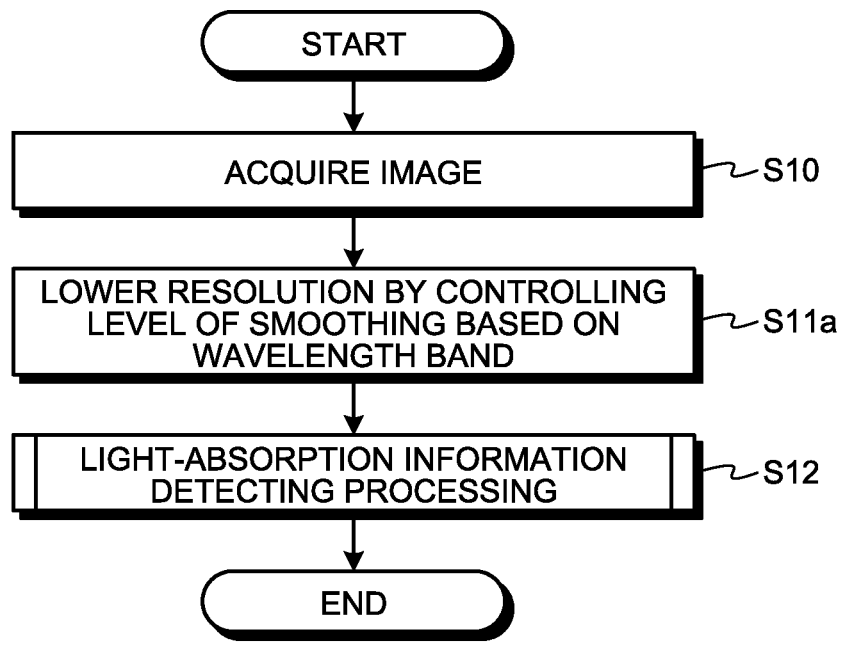
FIG. 21 is a flowchart illustrating an outline of processing executed by an image processing device according to a second modification example of the first embodiment of the disclosure.

FIG. 21 is a flowchart illustrating an outline of processing executed by an image processing device 1 according to the second modification example of the first embodiment of the disclosure. In FIG. 21, the image processing device 1 executes step S11a instead of step S11 in FIG. 2. Thus, only step S11a will be described in the following.

In step S11a, a low-resolution processing unit 8 control a level of smoothing (filter size) and lowers resolution on the basis of a wavelength band of each of a plurality of images acquired by an image acquiring unit 2 in step S10 described above. As a property of a narrowband image, detailed information is likely to appear in an image captured in a short wavelength, and detailed information becomes less likely to appear as a wavelength becomes longer. Thus, in the second modification example of the present first embodiment, a plurality of filter sizes is previously set for each wavelength band in such a manner that a filter size used for smoothing becomes smaller as a wavelength becomes shorter. Then, in a case where smoothing is performed, the low-resolution processing unit 8 selects and sets a filter size according to an image with the shortest wavelength in images resolution of which is to be lowered. In the second modification example of the present first embodiment, the low-resolution processing unit 8 performs smoothing of tentative light-absorption information of a [540] image by using a filter size set for a [415] image. After step S11a, the image processing device 1 transitions to step S12.

According to the above-described second modification example of the first embodiment of the disclosure, it is possible to reduce an influence of a case where there is different light-absorption information in a surrounding by changing a level of smoothing on the basis of a wavelength band. Thus, it is possible to improve accuracy in detection of light-absorption information at a certain depth in a living body.

Second Embodiment

Next, a second embodiment of the disclosure will be described. An image processing device according to the present second embodiment has a configuration different from that of the image processing device 1 according to the above-described first embodiment, and resolution lowering processing and light-absorption information detecting processing executed by the image processing device are different. More specifically, although only tentative light-absorption information of the [540] image is smoothed in the above-described first embodiment, tentative light-absorption information of each of a [415] image and a [540] image is smoothed in the present second embodiment. In the following, after a configuration of the image processing device according to the present second embodiment is described, resolution lowering processing and light-absorption information detecting processing executed by the image processing device will be described. Note that the same sign is assigned to a configuration identical to that of the image processing device 1 according to the first embodiment described above and a description thereof is omitted.

Configuration of Image Processing Device

Figure 22:
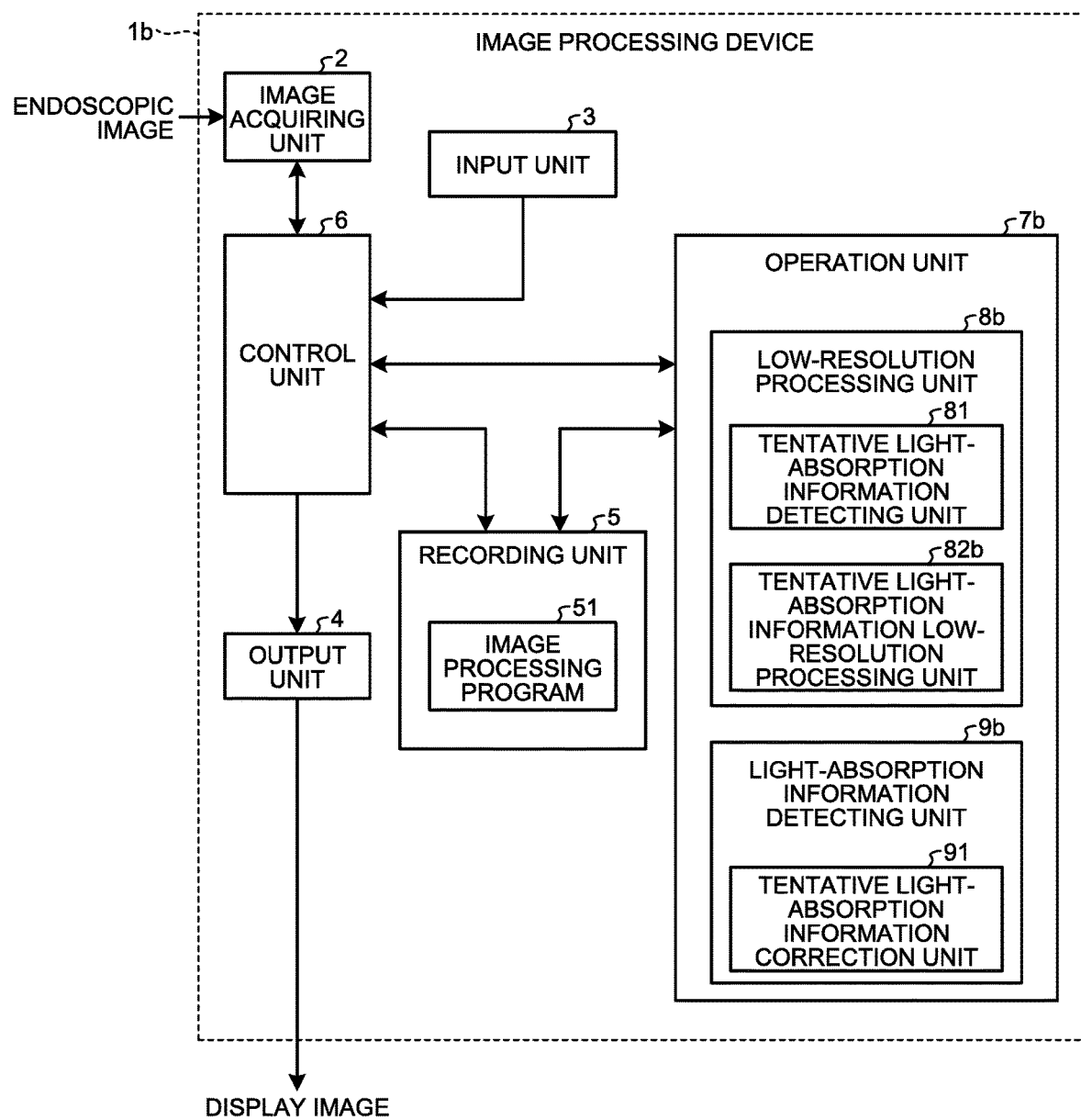
FIG. 22 is a block diagram illustrating a configuration of an image processing device according to a second embodiment of the disclosure.

FIG. 22 is a block diagram illustrating a configuration of the image processing device according to the second embodiment of the disclosure. An image processing device 1b illustrated in FIG. 22 includes an operation unit 7b instead of the operation unit 7 of the image processing device 1 according to the above-described first embodiment. The operation unit 7b includes a general-purpose processor such as a CPU or a special-purpose processor such as various operation circuits that are an ASIC, an FPGA, and the like and that execute a certain function.

Detailed Configuration of Operation Unit

Next, a detailed configuration of the operation unit 7b will be described.

The operation unit 7b includes a low-resolution processing unit 8b and a light-absorption information detecting unit 9b.

The low-resolution processing unit 8b generates a low-resolution image in which resolution of at least one image is lowered among a plurality of images that is acquired by an image acquiring unit 2 and that has different imaging time and different wavelength bands of light. The low-resolution processing unit 8b includes a tentative light-absorption information detecting unit 81 that detects tentative light-absorption information from an image in a certain wavelength band, and a tentative light-absorption information low-resolution processing unit 82b that lowers resolution of tentative light-absorption information.

The light-absorption information detecting unit 9b detects light-absorption information at a certain depth on the basis of a correlation between a correlation between a plurality of images at least including a low-resolution image and at least having wavelength bands different from each other. Also, the light-absorption information detecting unit 9b includes a tentative light-absorption information correction unit 91 that corrects tentative light-absorption information.

Resolution Lowering Processing

Figure 23:
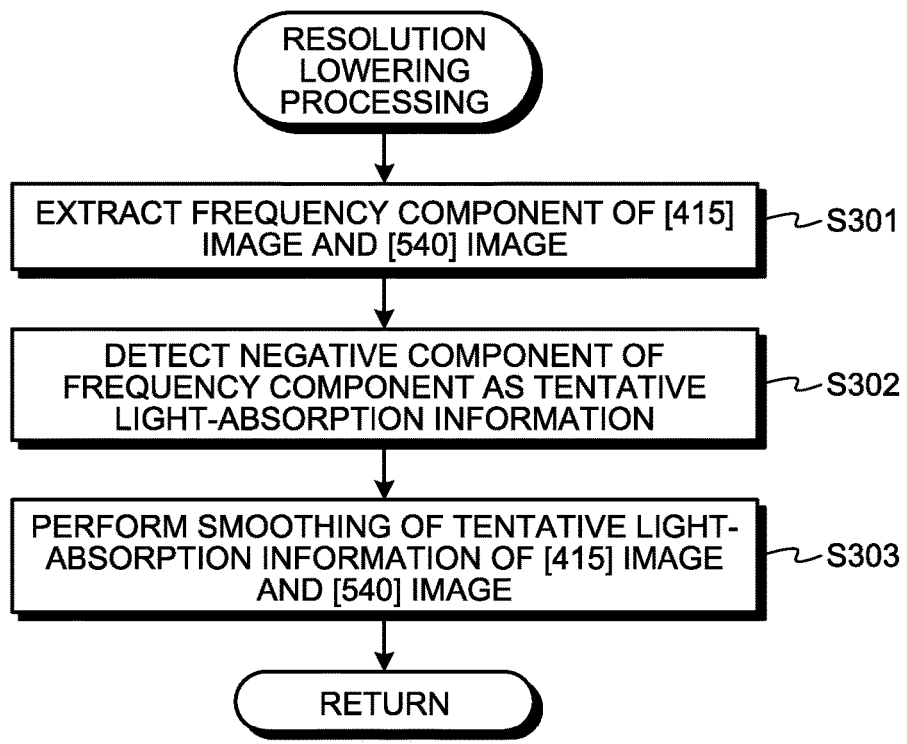
FIG. 23 is a flowchart illustrating an outline of resolution lowering processing executed by the image processing device according to the second embodiment of the disclosure.

Next, resolution lowering processing executed by the image processing device 1b will be described. FIG. 23 is a flowchart illustrating an outline of the resolution lowering processing executed by the image processing device 1b. Since step S301 and step S302 respectively correspond to step S111 and step S112 in FIG. 3 described above, a description thereof is omitted in FIG. 23.

In step S303, the tentative light-absorption information low-resolution processing unit 82b performs smoothing of tentative light-absorption information of each of a [415] image and a [540] image.

Figure 24:
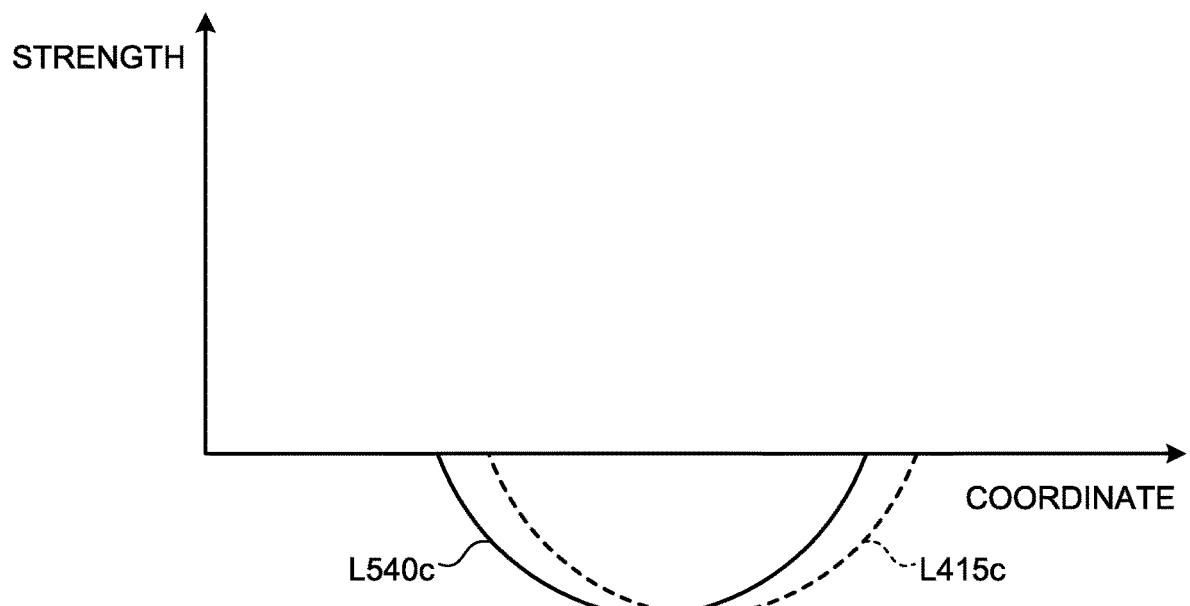
FIG. 24 is a view schematically illustrating a state in which tentative light-absorption information detected from each of a [415] image and a [540] image is smoothed by a tentative light-absorption information low-resolution processing unit according to the second embodiment of the disclosure.

FIG. 24 is a view schematically illustrating a state in which the tentative light-absorption information detected by the tentative light-absorption information low-resolution processing unit 82b from each of the [415] image and the [540] image is smoothed. In FIG. 24, a horizontal axis indicates a coordinate (pixel position), a vertical axis indicates strength, a curved line L415c indicates a state in which the tentative light-absorption information detected from the [415] image is smoothed, and a curved line L540c indicates a state in which the tentative light-absorption information detected from the [540] image is smoothed.

As indicated by the curved line L540c and the curved line L415c in FIG. 24, the tentative light-absorption information low-resolution processing unit 82b performs smoothing of the tentative light-absorption information of each of the [415] image and the [540] image. In the following description, a [415] image resolution of which is lowered is described as an α[415] image. After step S303, the image processing device 1b returns to the main routine in FIG. 2.

Light-Absorption Information Detecting Processing

Figure 25:
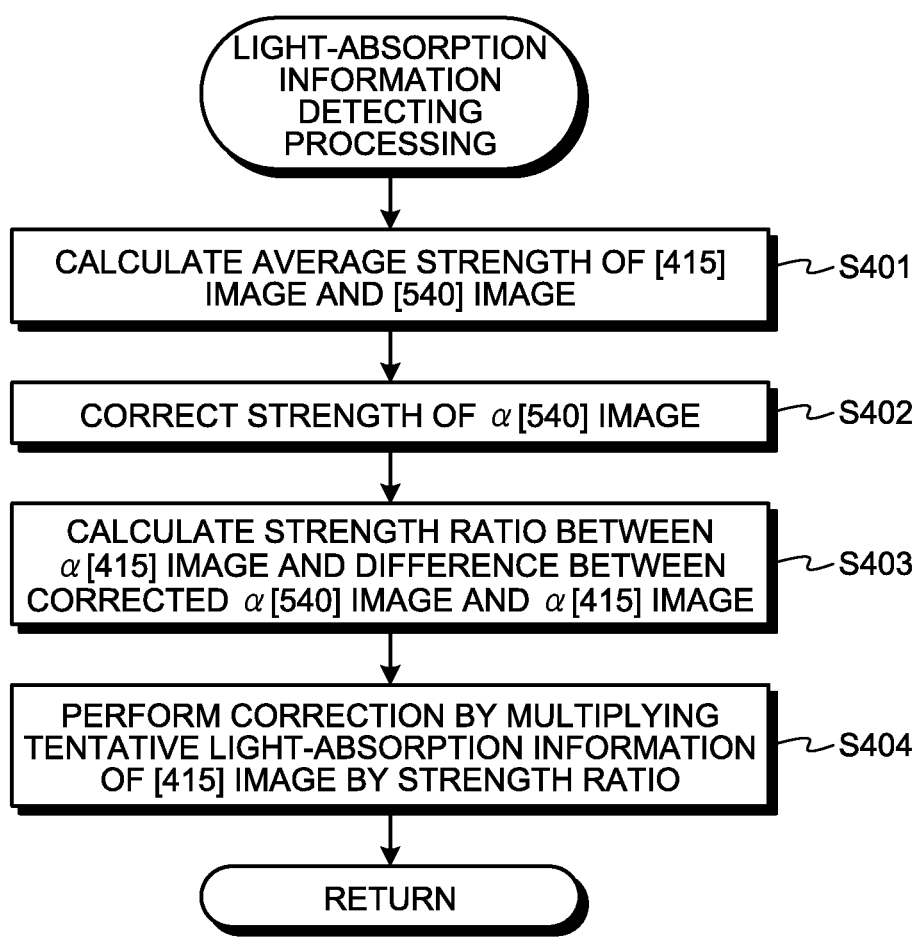
FIG. 25 is a flowchart illustrating an outline of light-absorption information detecting processing executed by the image processing device according to the second embodiment of the disclosure.

Next, the light-absorption information detecting processing executed by the image processing device 1b will be described. FIG. 25 is a flowchart illustrating an outline of the light-absorption information detecting processing executed by the image processing device 1b. Since step S401 and step S402 respectively correspond to step S121 and step S122 in FIG. 14 described above, a description thereof is omitted in FIG. 25.

In step S403, the tentative light-absorption information correction unit 91 calculates a difference acquired by subtraction of a corrected α[540] image from an α[415] image, and a strength ratio between a result of the subtraction and strength of the α[415] image.

Subsequently, the tentative light-absorption information correction unit 91 performs correction by multiplying the tentative light-absorption information of the [415] image, which information is calculated in FIG. 23 described above, by the strength ratio (step S404). In this case, the tentative light-absorption information correction unit 91 detects the tentative light-absorption information of the [415] image, which information is corrected by multiplication by the strength ratio, as light-absorption information at a certain depth in a living body, that is, light-absorption information in a surface layer from which information a middle-layer blood vessel is deleted.

According to the second embodiment of the disclosure described above, it is possible to reduce an influence of a positional deviation and to improve accuracy of detecting light-absorption information at a certain depth in a living body by performing correction with a correlation of light-absorption information resolution of which is lowered.

Third Embodiment

Next, the third embodiment of the disclosure will be described. An image processing device according to the present third embodiment has a configuration different from that of the image processing device 1 according to the above-described first embodiment, and executes different processing. In the following, after a configuration of the image processing device according to the present third embodiment is described, processing executed by the image processing device will be described. Note that the same sign is assigned to a configuration identical to that of the image processing device 1 according to the first embodiment described above and a description thereof is omitted.

Configuration of Image Processing Device

Figure 26:
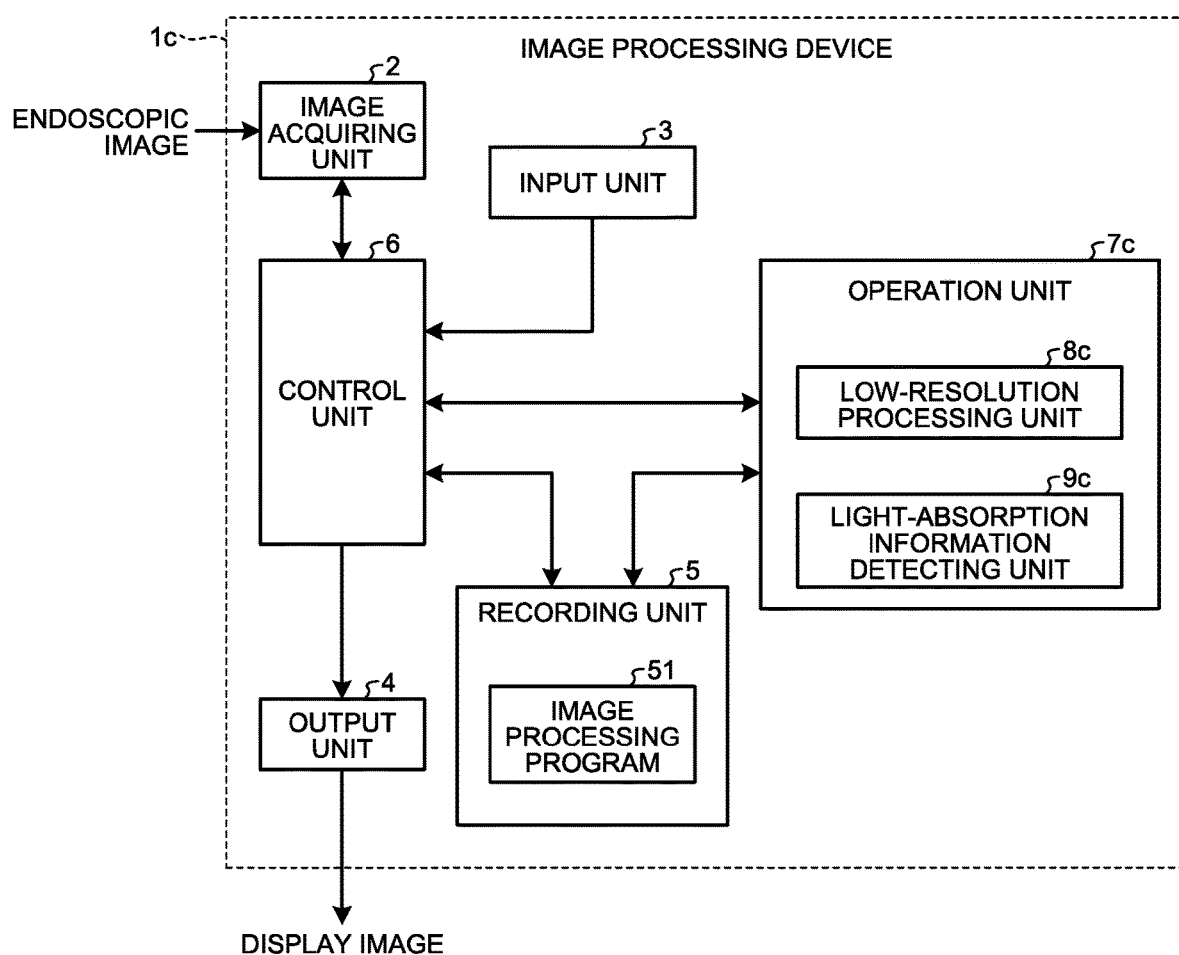
FIG. 26 is a block diagram illustrating a configuration of an image processing device according to a third embodiment of the disclosure.

FIG. 26 is a block diagram illustrating a configuration of the image processing device according to the third embodiment of the disclosure. An image processing device 1c illustrated in FIG. 26 includes an operation unit 7c instead of the operation unit 7 of the image processing device 1 according to the above-described first embodiment. The operation unit 7c includes a general-purpose processor such as a CPU or a special-purpose processor such as various operation circuits that are an ASIC, an FPGA, and the like and that execute a certain function.

Detailed Configuration of Operation Unit

Next, a detailed configuration of the operation unit 7c will be described.

The operation unit 7c includes a low-resolution processing unit 8c and a light-absorption information detecting unit 9c.

The low-resolution processing unit 8c lowers resolution by performing smoothing processing with respect to each of a [415] image and a [540] image that are acquired by an image acquiring unit 2 and that have different imaging time.

The light-absorption information detecting unit 9c subtracts a corrected α[540] image from an α[415] image resolution of which is lowered by the low-resolution processing unit 8c, and detects a negative component as light-absorption information.

Processing of Image Processing Device

FIG. 27 is a flowchart illustrating an outline of processing executed by the image processing device 1c. In FIG. 27, the image processing device 1c executes step S11c and step S12c instead of step S11 and step S12 in FIG. 2. Thus, step S11c and step S12c will be described in the following.

In step S11c, the low-resolution processing unit 8c performs smoothing processing with respect to the [415] image and the [540] image, and lowers resolution. In the following description, the [415] image resolution of which is lowered is described as an α[415] image, and the [540] image resolution of which is lowered is described as an α[540] image. Note that the smoothing processing is not a limitation, and the low-resolution processing unit 8c may lower resolution of an image, for example, by downsampling processing, resizing processing, or the like as long as resolution of an image can be lowered.

Subsequently, on the basis of the α[415] image and the α[540] image, the light-absorption information detecting unit 9c executes light-absorption information detecting processing to detect light-absorption information (step S12c). After step S12c, the image processing device 1c ends the present processing.

Light-Absorption Information Detecting Processing

FIG. 28 is a flowchart illustrating an outline of the light-absorption information detecting processing in step S12c in FIG. 27.

As illustrated in FIG. 28, the light-absorption information detecting unit 9c calculates average strength of each of the α[415] image and the α[540] image (step S501).

Subsequently, the light-absorption information detecting unit 9c corrects the average strength of the α[540] image (step S502). More specifically, the light-absorption information detecting unit 9c corrects strength of the α[540] image by multiplying the α[540] image by a ratio between the average strength of the α[415] image and the average strength of the α[540] image.

Subsequently, the light-absorption information detecting unit 9c calculates a difference between a corrected α[540] image and the α[415] image (step S503). More specifically, the light-absorption information detecting unit 9c subtracts the α[540] image, which is corrected in step S502, from the α[415] image and detects a negative component as light-absorption information. Note that the light-absorption information detecting unit 9c is not limited by the above-described method as long as light-absorption information can be detected on the basis of a correlation between images resolution of which is lowered. For example, after a ratio between the images resolution of which is lowered is calculated, a region equal to or smaller than a previously-set threshold with respect to a result of the calculation may be extracted and a ratio in this extracted region may be detected as light-absorption information. After step S503, the image processing device 1c returns to a main routine in FIG. 27.

According to the third embodiment of the disclosure described above, it is possible to reduce an influence of a positional deviation and to improve accuracy of detecting light-absorption information at a certain depth in a living body by performing correction with a correlation of light-absorption information resolution of which is lowered.

Different Embodiment

In the disclosure, an image processing program recorded in a recording unit can be realized by being executed by a computer system such as a personal computer or a work station. Also, such a computer system may be used by being connected to a device such as a different computer system or a server through a public line such as a local area network (LAN), a wide area network (WAN), or the Internet. In this case, an image processing device according to embodiments and modification examples thereof may acquire an image (image data) through these networks, may output a result of image processing to various output devices such as a viewer and a printer connected through these networks, or may store a result of image processing into a storage device, which is connected through these networks, such as a recording medium that can be read by a reading device connected to the networks, for example.

Note that although a context of processing between steps is expressed clearly with expressions such as "first," "then," and "subsequently," order of processing necessary for performance of the disclosure is not uniquely determined by these expressions. That is, order of processing in the flowcharts described in the present description can be changed within the scope of being consistent.

According to the disclosure, there is an effect that accuracy of detecting a blood vessel can be improved.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
    a processor comprising hardware, the processor being configured to:
        generate a low-resolution image by lowering resolution of at least one image in a plurality of images at a different imaging time which images are captured when illumination light in different wavelength bands is emitted, and
        detect light-absorption information at a certain depth based on a correlation between images which are in an image group including the low-resolution image and the plurality of images, and which are captured with the illumination light in the different wavelength bands, the correlation between the images being a correlation between an image in a certain wavelength band, and the low-resolution image in a wavelength band other than that of the image in the certain wavelength band,
    wherein the image in the certain wavelength band being an image in which the light-absorption information appears in the highest contrast.

2. An endoscope system comprising:
    an endoscope configured to generate image data by imaging an inside of a body of a subject when being inserted into the subject; and
    the image processing device according to claim 1, the image processing device being configured to execute image processing with respect to an endoscopic image corresponding to the image data generated by the endoscope.

3. An image processing device comprising:
a processor comprising hardware, the processor being configured to
   generate a low-resolution image by lowering resolution of at least one image in a plurality of images at a different imaging time which images are captured when illumination light in different wavelength bands is emitted,
   detect tentative light-absorption information from an image in a certain wavelength band,
   detect light-absorption information at a certain depth based on a correlation between images which are in an image group including the low-resolution image and the plurality of images, which are captured with the illumination light in the different wavelength bands, and at least one of which is the low-resolution image, and
   correct the tentative light-absorption information based on the correlation between the images,
wherein the image in the certain wavelength band being an image in which the light-absorption information appears in the highest contrast.

4. An endoscope system comprising:
an endoscope configured to generate image data by imaging an inside of a body of a subject when being inserted into the subject; and
the image processing device according to claim 3, the image processing device being configured to execute image processing with respect to an endoscopic image corresponding to the image data generated by the endoscope.

5. An image processing method comprising:
acquiring a plurality of images at a different imaging time which images are captured when illumination light in different wavelength bands is emitted;
generating a low-resolution image by lowering resolution of at least one image in the plurality of images; and
detecting light-absorption information at a certain depth based on a correlation between images which are in an image group including the low-resolution image and the plurality of images, and which are captured with illumination light in the different wavelength bands, the correlation between the images being a correlation between an image in a certain wavelength band, and the low-resolution image in a wavelength band other than that of the image in the certain wavelength band, the image in the certain wavelength band being an image in which the light-absorption information appears in the highest contrast.

6. An image processing method comprising:
acquiring a plurality of images at a different imaging time which images are captured when illumination light in different wavelength bands is emitted;
generating a low-resolution image by lowering resolution of at least one image in the plurality of images; and
detecting tentative light-absorption information from an image in a certain wavelength band,
detecting light-absorption information at a certain depth based on a correlation between images which are in an image group including the low-resolution image and the plurality of images, which are captured with illumination light in the different wavelength bands, and at least one of which is the low-resolution image, and
correcting the tentative light-absorption information based on the correlation between the images, the image in the certain wavelength band being an image in which the light-absorption information appears in the highest contrast.

* * * * *